(12) United States Patent
Huang et al.

(10) Patent No.: US 12,299,100 B2
(45) Date of Patent: May 13, 2025

(54) IDENTIFICATION DEVICE, IDENTIFICATION SYSTEM, IDENTIFICATION METHOD, AND PROGRAM RECORDING MEDIUM USING A WALKING WAVEFORM OF A USER

(71) Applicant: NEC Corporation, Tokyo (JP)

(72) Inventors: Chenhui Huang, Tokyo (JP); Kenichiro Fukushi, Tokyo (JP); Zhenwei Wang, Tokyo (JP); Fumiyuki Nihey, Tokyo (JP)

(73) Assignee: NEC CORPORATION, Tokyo (JP)

( * ) Notice: Subject to any disclaimer, the term of this patent is extended or adjusted under 35 U.S.C. 154(b) by 195 days.

(21) Appl. No.: 18/015,876

(22) PCT Filed: Jul. 22, 2020

(86) PCT No.: PCT/JP2020/028346
§ 371 (c)(1),
(2) Date: Jan. 12, 2023

(87) PCT Pub. No.: WO2022/018837
PCT Pub. Date: Jan. 27, 2022

(65) Prior Publication Data
US 2023/0259595 A1    Aug. 17, 2023

(51) Int. Cl.
G06F 21/32    (2013.01)
A61B 5/00    (2006.01)
A61B 5/11    (2006.01)

(52) U.S. Cl.
CPC .............. *G06F 21/32* (2013.01); *A61B 5/112* (2013.01); *A61B 5/7235* (2013.01)

(58) Field of Classification Search
CPC ........ G06F 21/32; A61B 5/112; A61B 5/7235
(Continued)

(56) References Cited

U.S. PATENT DOCUMENTS 6,836,744 B1 * 12/2004 Asphahani ............... A43D 1/02
702/141
2002/0138743 A1 * 9/2002 Murakami ............. G07C 9/257
713/186
(Continued)

FOREIGN PATENT DOCUMENTS

JP    2004-344418 A    12/2004
JP    2005-078228 A    3/2005
(Continued)

OTHER PUBLICATIONS

International Search Report for PCT Application No. PCT/JP2020/028346, mailed on Oct. 6, 2020.
(Continued)

*Primary Examiner* — Thanh T Le
(74) *Attorney, Agent, or Firm* — Sughrue Mion, PLLC

(57) ABSTRACT

Provided is an identification device for identifying an individual on the basis of gait irrespective of the type of footwear, the identification device comprising a detection unit that detects a walking event on the basis of a walking waveform of a user, a waveform processing unit that normalizes the walking waveform on the basis of the detected walking event and generates a normalized waveform, and an identification unit that identifies the user on the basis of the normalized waveform.

8 Claims, 23 Drawing Sheets

(58) Field of Classification Search
USPC .......................................................... 713/186
See application file for complete search history.

(56) References Cited

U.S. PATENT DOCUMENTS

| | | | | |
|---|---|---|---|---|
| 2013/0200996 | A1* | 8/2013 | Gray | G05B 1/00 340/5.52 |
| 2015/0276793 | A1* | 10/2015 | Takenaka | A61B 5/1121 73/504.03 |
| 2016/0147841 | A1* | 5/2016 | Gray | A43B 3/34 600/595 |
| 2017/0142501 | A1* | 5/2017 | Jakobsson | A61B 5/1112 |
| 2018/0078179 | A1* | 3/2018 | Deng | H04W 12/065 |
| 2018/0089280 | A1* | 3/2018 | Gray | A43B 3/34 |
| 2018/0089408 | A1* | 3/2018 | Cheung | G06F 21/32 |
| 2019/0147154 | A1* | 5/2019 | Das | G06Q 30/0185 726/21 |
| 2019/0213193 | A1* | 7/2019 | Gray | G06F 16/24575 |
| 2019/0353501 | A1* | 11/2019 | Ozawa | A61B 5/112 |
| 2021/0137467 | A1* | 5/2021 | Aoki | A61B 5/082 |
| 2021/0291788 | A1* | 9/2021 | Nawa | H04W 12/06 |
| 2021/0291789 | A1* | 9/2021 | Nawa | H04W 12/06 |
| 2021/0295623 | A1* | 9/2021 | Nawa | G08C 17/02 |
| 2021/0393166 | A1* | 12/2021 | DeMers | A61B 5/1126 |
| 2022/0142850 | A1* | 5/2022 | Ahn | G16H 20/30 |
| 2022/0147611 | A1* | 5/2022 | Nishimura | G06F 21/44 |
| 2022/0362654 | A1* | 11/2022 | Xu | G01P 15/18 |
| 2023/0034341 | A1* | 2/2023 | Huang | A61B 5/11 |
| 2023/0137878 | A1* | 5/2023 | Kurata | G07C 9/00182 705/39 |
| 2023/0286463 | A1* | 9/2023 | Matsuzawa | B60R 25/31 |
| 2023/0346262 | A1* | 11/2023 | Finch | A61B 5/1124 |

FOREIGN PATENT DOCUMENTS

| | | |
|---|---|---|
| JP | 2006-087735 A | 4/2006 |
| JP | 2008-250996 A | 10/2008 |
| JP | 2015-153143 A | 8/2015 |
| JP | 2018-042745 A | 3/2018 |

OTHER PUBLICATIONS

English translation of Written opinion for PCT Application No. PCT/JP2020/028346, mailed on Oct. 6, 2020.

* cited by examiner

IDENTIFICATION DEVICE, IDENTIFICATION SYSTEM, IDENTIFICATION METHOD, AND PROGRAM RECORDING MEDIUM USING A WALKING WAVEFORM OF A USER

This application is a National Stage Entry of PCT/JP2020/028346 filed on Jul. 22, 2020, the contents of all of which are incorporated herein by reference, in their entirety.

TECHNICAL FIELD

The present disclosure relates to an identification device or the like that identifies an individual based on a gait.

BACKGROUND ART

A device for analyzing a gait of a user by mounting a load measurement device or an inertial measurement device on footwear such as shoes has been developed. In a case where an individual can be identified based on a gait, personal authentication can be performed without using hardware such as fingerprint authentication hardware.

PTL 1 discloses a personal authentication system that determines whether an authentication target person is a specific person based on a load on a sole of a foot of a person. The system of PTL 1 generates, based on a load on a sole of a foot of a person, load information indicating a change over time in load applied to the sole of the foot at the time of walking. The system of PTL 1 determines whether an authentication target person is a specific person based on the load information of the authentication target person and determination information stored in advance.

CITATION LIST

Patent Literature

[PTL 1] JP 2008-250996 A

SUMMARY OF INVENTION

Technical Problem

In the method of PTL 1, it is necessary to measure a load on a sole of a foot of a person who is walking. In a case of using a change over time in load applied to a sole of a foot, since a difference occurs in a waveform depending on a type of footwear worn by a user, it has been difficult to identify an individual with sufficient accuracy.

An object of the present disclosure is to provide an identification device or the like that can identify an individual based on a gait regardless of a type of footwear.

Solution to Problem

An identification device according to one aspect of the present disclosure includes: a detection unit that detects a walking event from a walking waveform of a user; a waveform processing unit that normalizes the walking waveform based on the detected walking event to generate a normalized waveform; and an identification unit that identifies the user based on the normalized waveform.

An identification method according to one aspect of the present disclosure is executed by a computer, the identification method including: detecting a walking event from a walking waveform of a user; normalizing the walking waveform based on the detected walking event to generate a normalized waveform; and identifying the user based on the normalized waveform.

A program according to the present disclosure causes a computer to execute: processing of detecting a walking event from a walking waveform of a user; processing of normalizing the walking waveform based on the detected walking event to generate a normalized waveform; and processing of identifying the user based on the normalized waveform.

Advantageous Effects of Invention

According to the present disclosure, it is possible to provide an identification device or the like that can identify an individual based on a gait regardless of a type of footwear.

EXAMPLE EMBODIMENT

Hereinafter, example embodiments of the present invention will be described with reference to the drawings. However, the example embodiments described below have technically preferable limitations for carrying out the present invention, but the scope of the invention is not limited to the following. In all the drawings used in the following description of the example embodiments, the same reference signs are given to the same parts unless there is a particular reason. Further, in the following example embodiments, repeated description of similar configurations/operations may be omitted.

First Example Embodiment

First, an identification system according to the present example embodiment will be described with reference to the drawings. The identification system according to the present example embodiment performs personal identification by measuring a feature (also referred to as a gait) included in a walking pattern of a user and analyzing the measured gait. Hereinafter, the "user" means an identification target person of the identification system according to the present example embodiment.

Figure 1:
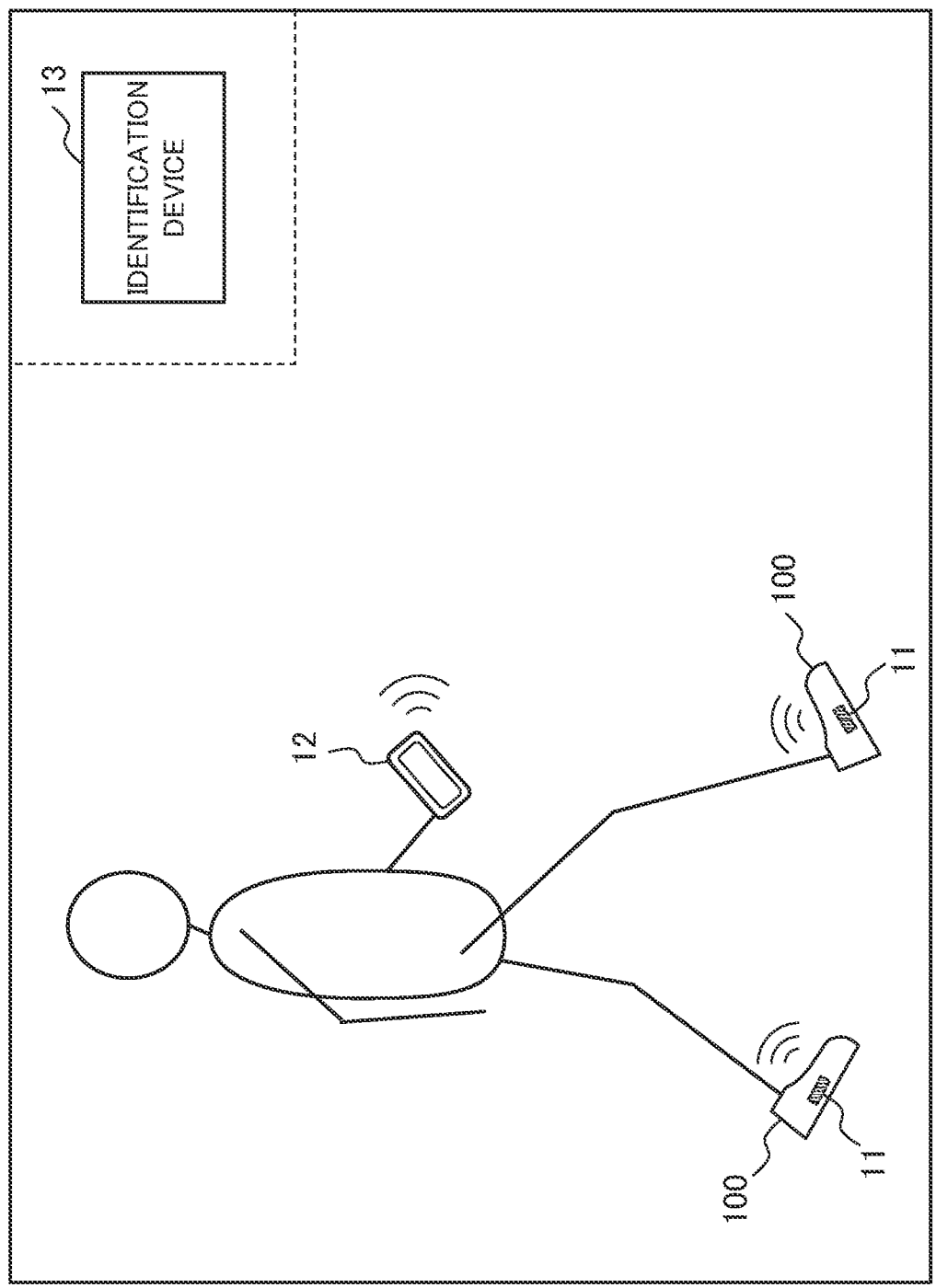
FIG. 1 is a conceptual diagram illustrating an example of a configuration of an identification system according to a first example embodiment.

FIG. 1 is a conceptual diagram for explaining an overall configuration of the identification system according to the present example embodiment. The identification system according to the present example embodiment includes a data acquisition device 11, a mobile terminal 12, and an identification device 13.

The data acquisition device 11 is installed in footwear such as a shoe 100. The data acquisition device 11 includes an acceleration sensor and an angular velocity sensor. The data acquisition device 11 measures physical quantities such as an acceleration and an angular velocity acquired by the acceleration sensor and the angular velocity sensor as physical quantities related to a motion of the foot of the user wearing the footwear such as the shoe 100. The physical quantities related to the motion of the foot measured by the data acquisition device 11 includes not only the acceleration and the angular velocity but also a velocity and an angle calculated by integrating the acceleration and the angular velocity. The data acquisition device 11 converts the measured physical quantity into digital data (also referred to as sensor data). The data acquisition device 11 transmits the converted sensor data to the mobile terminal 12. The data acquisition device 11 transmits the sensor data to the identification device 13 via the mobile terminal 12.

The data acquisition device 11 is implemented by, for example, an inertial measurement device including an acceleration sensor and an angular velocity sensor. Examples of the inertial measurement device include an inertial measurement unit (IMU). The IMU includes a three-axis acceleration sensor and a three-axis angular velocity sensor. Examples of the inertial measurement device further include a vertical gyro (VG), an attitude and heading reference system (AHRS), and a global positioning system/inertial navigation system (GPS/INS).

Figure 2:
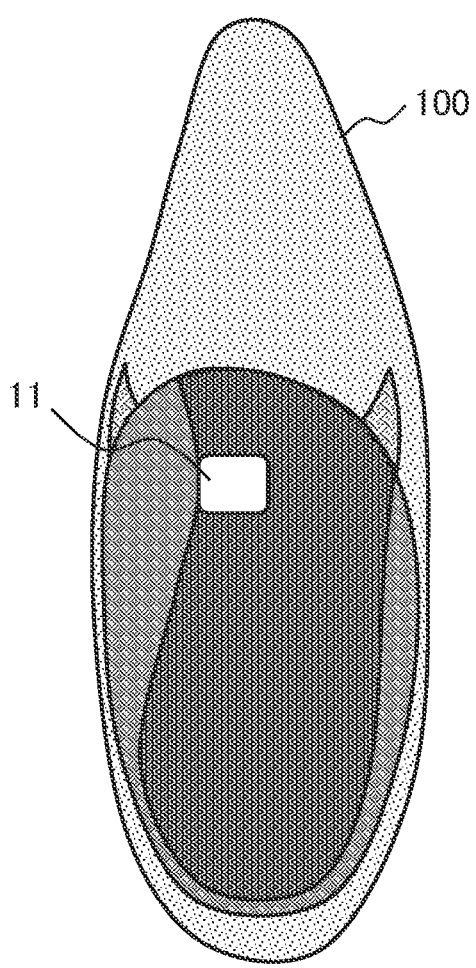
FIG. 2 is a conceptual diagram illustrating an example in which a data acquisition device of the identification system according to the first example embodiment is arranged in footwear.

FIG. 2 is a conceptual diagram illustrating an example in which the data acquisition device 11 is installed in the shoe 100. In the example of FIG. 2, the data acquisition device 11 is installed at a position that comes into contact with a back side of an arch of the foot. For example, the data acquisition device 11 is installed at an insole inserted into the shoe 100. For example, the data acquisition device 11 is installed at a bottom surface of the shoe 100. For example, the data acquisition device 11 is embedded in a main body of the shoe 100. The data acquisition device 11 may be detachable from the shoe 100 or does not have to be detachable from the shoe 100. The data acquisition device 11 may be installed at a position other than the back side of the arch of the foot as long as the sensor data regarding the motion of the foot can be acquired. Furthermore, the data acquisition device 11 may be installed at a sock worn by the user or a decorative article such as an anklet worn by the user. Alternatively, the data acquisition device 11 may be directly attached to the foot or may be embedded in the foot. FIG. 2 illustrates an example in which the data acquisition device 11 is installed in the shoe 100 for the right foot, but the data acquisition device 11 may be installed in the shoes 100 for both feet. In a case where the data acquisition device 11 is installed in the shoes 100 for both feet, it is possible to identify the user based on the motions of both feet.

Figure 3:
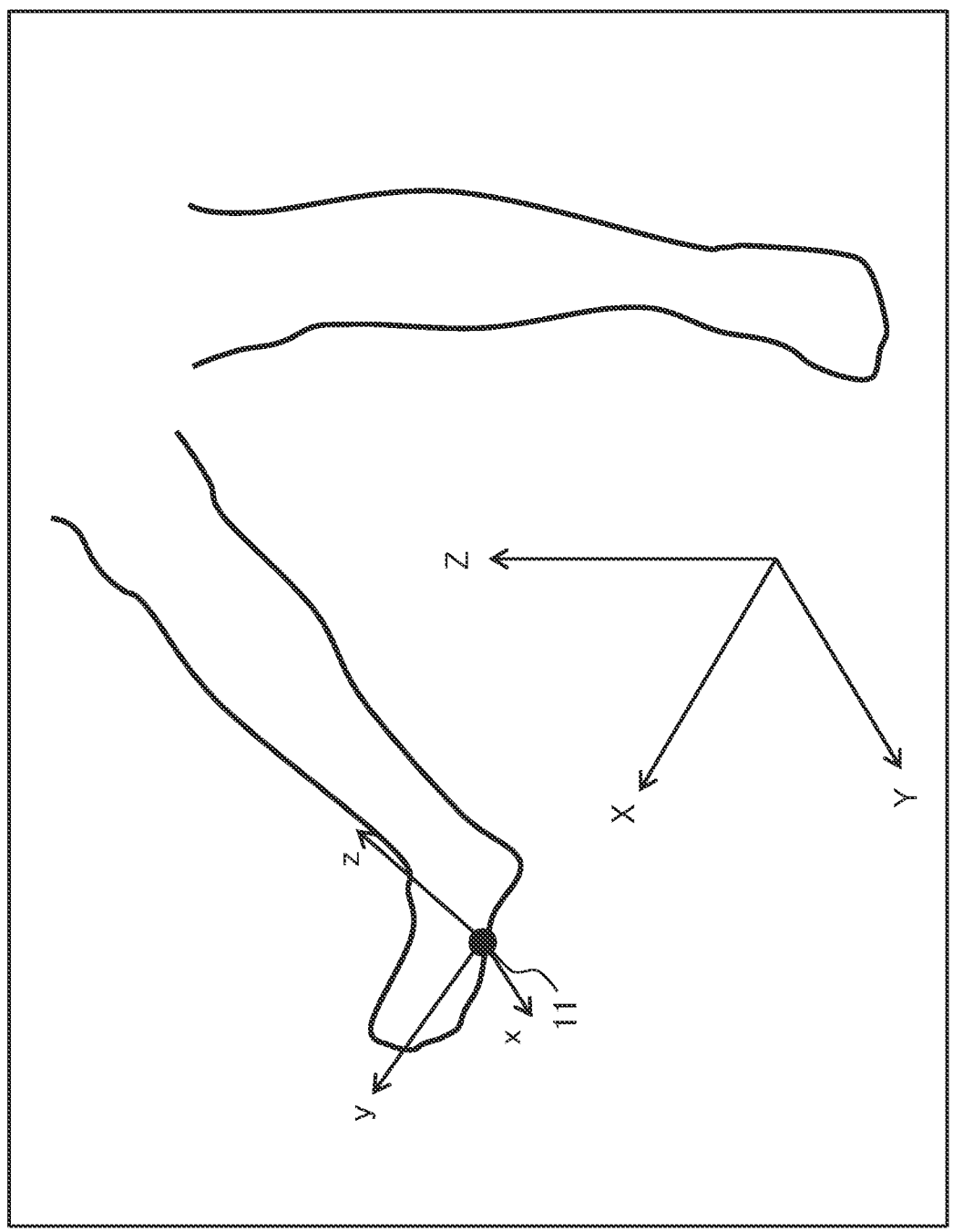
FIG. 3 is a conceptual diagram for explaining a local coordinate system and a world coordinate system of the data acquisition device of the identification system according to the first example embodiment.

FIG. 3 is a conceptual diagram for explaining a local coordinate system (x axis, y axis, and z axis) set in the data acquisition device 11 and a world coordinate system (X axis, Y axis, and Z axis) set with respect to the ground in a case where the data acquisition device 11 is installed at the back side of the arch of foot. In the world coordinate system (X axis, Y axis, and Z axis), in a state where the user is standing upright, a lateral direction of the user is set to an X-axis direction (a rightward direction is a positive direction), a front direction of the user (traveling direction) is set to a Y-axis direction (a forward direction is a positive direction), and a gravity direction is set to a Z-axis direction (a vertically upward direction is a positive direction). Furthermore, in the present example embodiment, a local coordinate system including an x direction, a y direction, and a z direction with respect to the data acquisition device 11 is set. In the present example embodiment, rotation around the x-axis is defined as pitch, rotation around the y-axis is defined as roll, and rotation around the z-axis is defined as yaw.

The mobile terminal 12 is a communication device that can be carried by the user. For example, the mobile terminal 12 is a portable communication device having a communication function, such as a smartphone, a smart watch, or a mobile phone. The mobile terminal 12 receives the sensor data regarding the motion of the foot of the user from the data acquisition device 11. The mobile terminal 12 transmits the received sensor data to a server or the like on which the identification device 13 is mounted. The function of the identification device 13 may be implemented by a program or the like installed in the mobile terminal 12. In this case, the mobile terminal 12 processes the received sensor data by a program or the like installed therein.

The identification device 13 is mounted on a server (not illustrated) or the like. For example, the identification device 13 may be implemented by an application server. For example, the identification device 13 may be implemented by a program or the like installed in the mobile terminal 12. The identification device 13 receives the sensor data regarding the motion of the foot of the user from the mobile terminal 12. The identification device 13 detects a predetermined walking event from a waveform (also referred to as a walking waveform) based on time-series data of the received sensor data.

The identification device 13 normalizes the walking waveform based on the walking event detected from the walking waveform. For example, the identification device 13 cuts out a walking waveform for one gait cycle based on the detected walking event. The identification device 13 divides the cut-out walking waveform based on the walking event. The identification device 13 normalizes each divided walking waveform (also referred to as divided waveform). The identification device 13 integrates the normalized divided waveforms to generate a normalized walking waveform (also referred to as a normalized waveform) for one gait cycle.

The identification device 13 identifies the user based on the normalized waveform. For example, the identification device 13 identifies the user by using a trained model that has learned a feature extracted from the normalized waveform of each user. The identification device 13 uses the trained model that has learned the feature extracted from the normalized waveform. It is sufficient if the trained model is generated at the time of factory shipment of a product, calibration before the user uses the identification device 13, or the like.

Data Acquisition Device

Figure 4:
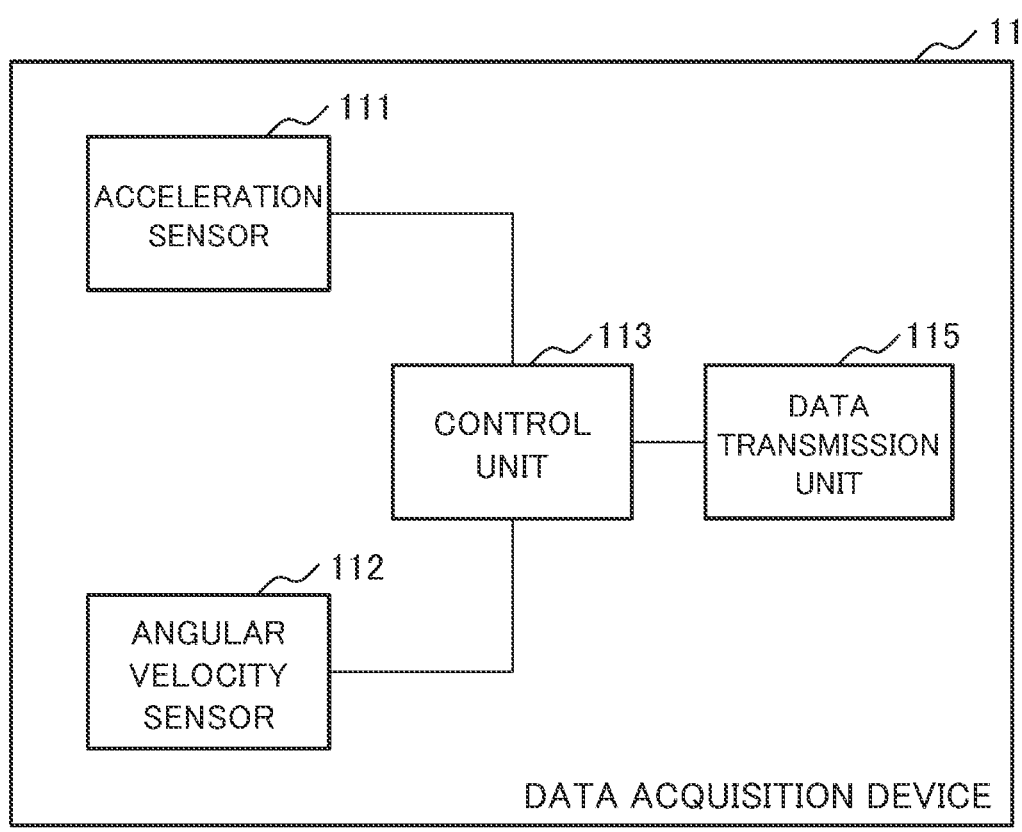
FIG. 4 is a block diagram illustrating an example of a configuration of the data acquisition device of the identification system according to the first example embodiment.

Next, details of the data acquisition device 11 will be described with reference to the drawings. FIG. 4 is a block diagram illustrating an example of a detailed configuration of the data acquisition device 11. The data acquisition device 11 includes an acceleration sensor 111, an angular velocity sensor 112, a control unit 113, and a data transmission unit 115. The data acquisition device 11 further includes a power supply (not illustrated). In the following description, each of the acceleration sensor 111, the angular velocity sensor 112, the control unit 113, and the data transmission unit 115 will be described as an operation subject, but the data acquisition device 11 may be regarded as the operation subject.

The acceleration sensor 111 is a sensor that measures accelerations in three axial directions. The acceleration sensor 111 outputs the measured acceleration to the control unit 113. For example, a piezoelectric sensor, a piezoresistive sensor, a capacitive sensor, or the like can be used as the acceleration sensor 111. A measurement method of the sensor used as the acceleration sensor 111 is not limited as long as the sensor can measure an acceleration.

The angular velocity sensor 112 is a sensor that measures angular velocities in the three axial directions. The angular velocity sensor 112 outputs the measured angular velocities to the control unit 113. For example, a vibration sensor, a capacitive sensor, or the like can be used as the angular velocity sensor 112. A measurement method of the sensor used as the angular velocity sensor 112 is not limited as long as the sensor can measure an angular velocity.

The control unit 113 acquires the accelerations and the angular velocities in the three axial directions from the acceleration sensor 111 and the angular velocity sensor 112. The control unit 113 converts the acquired acceleration and angular velocity into digital data, and outputs the converted digital data (also referred to as the sensor data) to the data transmission unit 115. The sensor data includes at least acceleration data (including acceleration vectors in the three axial directions) obtained by converting an acceleration of analog data into digital data and angular velocity data (including angular velocity vectors in the three axial directions) obtained by converting angular velocity of analog data into digital data. Times at which the acceleration data and the angular velocity data are acquired are associated with the acceleration data and the angular velocity data. Furthermore, the control unit 113 may be configured to output sensor data obtained by applying correction such as a mounting error correction, temperature correction, and linearity correction to the acquired acceleration data and angular velocity data. The control unit 113 may generate angle data in the three axial directions by using the acquired acceleration data and angular velocity data.

For example, the control unit 113 is a microcomputer or a microcontroller that performs overall control of the data acquisition device 11 and data processing. For example, the control unit 113 includes a central processing unit (CPU), a random access memory (RAM), a read only memory (ROM), a flash memory, and the like. The control unit 113 controls the acceleration sensor 111 and the angular velocity sensor 112 to measure the angular velocity and the acceleration. For example, the control unit 113 performs analog-to-digital conversion (AD conversion) on the physical quantities (analog data) such as the measured angular velocity and acceleration, and stores converted digital data in the flash memory. The physical quantities (analog data) measured by the acceleration sensor 111 and the angular velocity sensor 112 may be converted into digital data in the acceleration sensor 111 and the angular velocity sensor 112. The digital data stored in the flash memory is output to the data transmission unit 115 at a predetermined timing.

The data transmission unit 115 acquires the sensor data from the control unit 113. The data transmission unit 115 transmits the acquired sensor data to the mobile terminal 12. The data transmission unit 115 may transmit the sensor data to the mobile terminal 12 via a wire such as a cable, or may transmit the sensor data to the mobile terminal 12 via wireless communication. For example, the data transmission unit 115 transmits the sensor data to the mobile terminal 12 via a wireless communication function (not illustrated) conforming to a protocol such as Bluetooth (registered trademark) or WiFi (registered trademark). The communication function of the data transmission unit 115 may also conform to a protocol other than Bluetooth (registered trademark) or WiFi (registered trademark).

Identification Device

Figure 5:
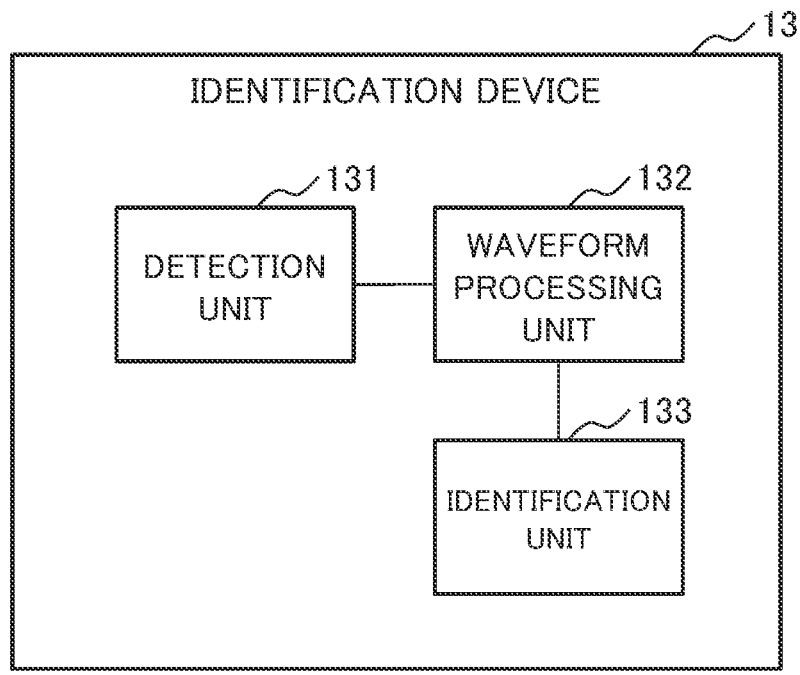
FIG. 5 is a block diagram illustrating an example of a configuration of an identification device of the identification system according to the first example embodiment.

Next, details of the identification device 13 will be described with reference to the drawings. FIG. 5 is a block diagram illustrating an example of a detailed configuration of the identification device 13. The identification device 13 includes a detection unit 131, a waveform processing unit 132, and an identification unit 133.

The detection unit 131 acquires the sensor data acquired by the data acquisition device 11 from the mobile terminal 12. The detection unit 131 converts the coordinate system of the acquired sensor data from the local coordinate system to the world coordinate system. When the user is standing upright, the local coordinate system (x axis, y axis, and z axis) and the world coordinate system (X axis, Y axis, and Z axis) match each other. When the user is walking, since a spatial orientation of the data acquisition device 11 changes, the local coordinate system (x axis, y axis, and z axis) and the world coordinate system (X axis, Y axis, and Z axis) do not match each other. Therefore, the detection unit 131 converts the coordinate system of the sensor data acquired by the data acquisition device 11 from the local coordinate system (x axis, y axis, and z axis) of the data acquisition device 11 to the world coordinate system (X axis, Y axis, and Z axis).

Figure 6:
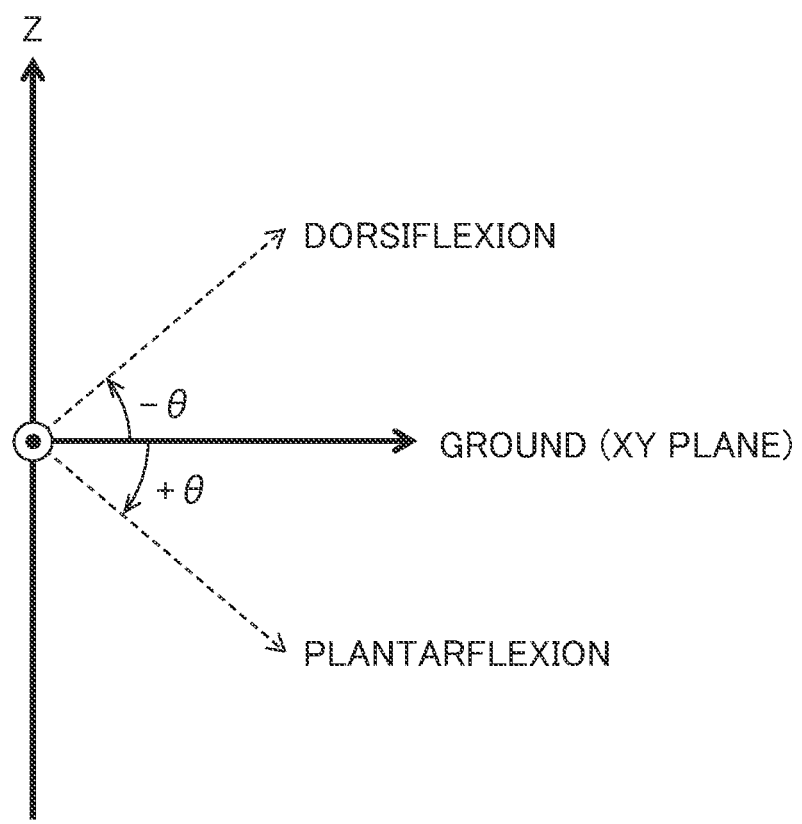
FIG. 6 is a conceptual diagram for explaining a plantar angle generated by the data acquisition device of the identification system according to the first example embodiment.

The detection unit 131 generates a walking waveform by using the sensor data whose coordinate system is converted to the world coordinate system. For example, the detection unit 131 generates walking waveforms related to accelerations, angular velocities, and angles in the three axial directions. For example, the detection unit 131 generates a walking waveform of an angle of the sole (also referred to as a plantar angle) with respect to the ground by using the acceleration and the angular velocity. FIG. 6 is a conceptual diagram for explaining the plantar angle calculated by the detection unit 131. The plantar angle is an angle of the sole with respect to the ground (XY plane), and is also referred to as a posture angle. In the present example embodiment, a positive angle and a negative angle of the plantar angle are defined in such a way that a state in which the toe is located above the heel (dorsiflexion) is negative, and a state in which the toe is located below the heel (plantarflexion) is positive.

For example, the detection unit 131 calculates the plantar angle by using the acceleration in each of an X-axis direction and a Y-axis direction. For example, the detection unit 131 may calculate the angle around each of the X axis, the Y axis, and the Z axis by integrating the values of the angular velocities around the X axis, the Y axis, and the Z axis. The acceleration data and the angular velocity data include high-frequency and low-frequency noises that change in various directions. Therefore, the detection unit 131 may apply a low-pass filter and a high-pass filter to the acceleration data and the angular velocity data to remove a high-frequency component and a low-frequency component. As the high frequency component and the low frequency component are removed, accuracy of the sensor data on which noise easily occurs can be improved. In addition, the detection unit 131 may apply a complementary filter to each of the acceleration data and the angular velocity data to take a weighted average. It is possible to improve the accuracy of the sensor data by applying the complementary filter and taking the weighted average.

Figure 7:
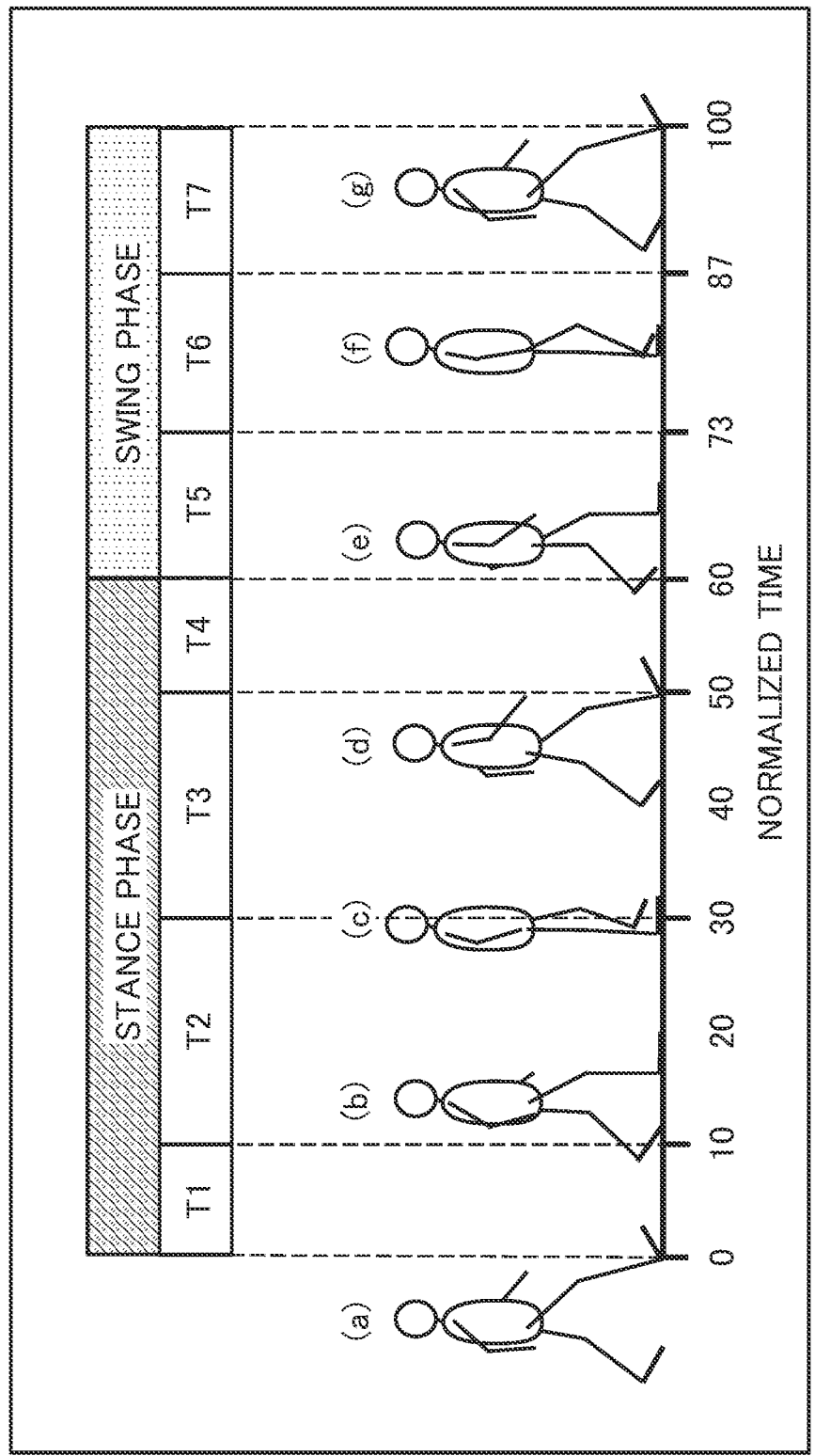
FIG. 7 is a conceptual diagram for explaining general walking.

FIG. 7 is a conceptual diagram for explaining a general gait cycle. FIG. 7 illustrates one gait cycle of the right foot. The horizontal axis in FIG. 7 represents a time (also referred to as normalized time) normalized with one gait cycle of the right foot as 100%, in which a time point at which the heel of the right foot lands on the ground is a start point, and a time point at which the heel of the right foot next lands on the ground is an end point. In general, one gait cycle of one foot is roughly divided into a stance phase in which at least a part of a back side of the foot is in contact with the ground and a swing phase in which the back side of the foot is away from the ground. The stance phase is further subdivided into an initial stance period T1, a mid-stance period T2, a terminal stance period T3, and a pre-swing period T4. The swing phase is further subdivided into an initial swing period T5, a mid-swing period T6, and a terminal swing period T7.

In FIG. 7, (a) illustrates a state in which the heel of the right foot is in contact with the ground (heel contact). (b) illustrates a state in which the toe of the left foot is separated from the ground in a state in which the entire sole of the right foot is in contact with the ground (opposite toe off). (c) illustrates a state in which the heel of the right foot is lifted in a state in which the entire sole of the right foot is in contact with the ground (heel rise). (d) illustrates a state in which the heel of the left foot is in contact with the ground (opposite heel contact). (e) illustrates a state in which the toe of the right foot is separated from the ground in a state in which the entire sole of the left foot is in contact with the ground (toe off). (f) illustrates a state in which the left foot and the right foot cross each other in a state where the entire sole of the left foot is in contact with the ground (foot crossing). (g) illustrates a state in which the heel of the right foot is in contact with the ground (heel contact).

Figure 8:
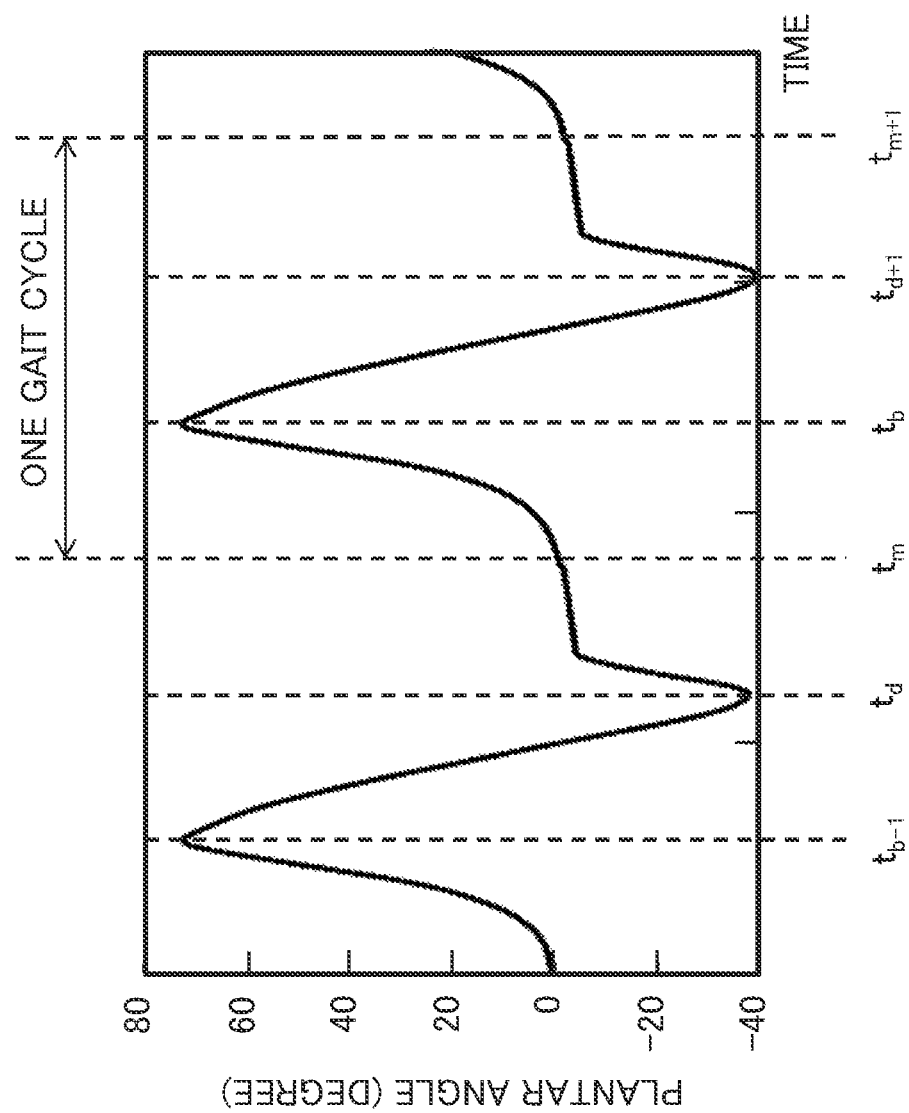
FIG. 8 is a graph for explaining a walking waveform of a plantar angle generated by the identification device of the identification system according to the first example embodiment.

FIG. 8 is a graph for explaining a walking waveform (plantar angle) for one gait cycle. A time $t_d$ at which the walking waveform is minimized corresponds to a timing of the start of the stance phase. A time $t_b$ at which the walking waveform is maximized corresponds to a timing of the start of the swing phase. A time at the midpoint between the time $t_d$ of the start of the stance phase and the time $t_b$ of the start of the swing phase corresponds to a center timing of the stance phase. In the present example embodiment, the time corresponding to the center timing of the stance phase is set to a time of the start point of one gait cycle (also referred to as a start point time $t_m$). In the present example embodiment, a time corresponding to a center timing of a stance phase next to the stance phase of the timing of the start point time $t_m$ is set to a time of the end point of one gait cycle (also referred to as an end point time $t_{m+1}$).

Figure 9:
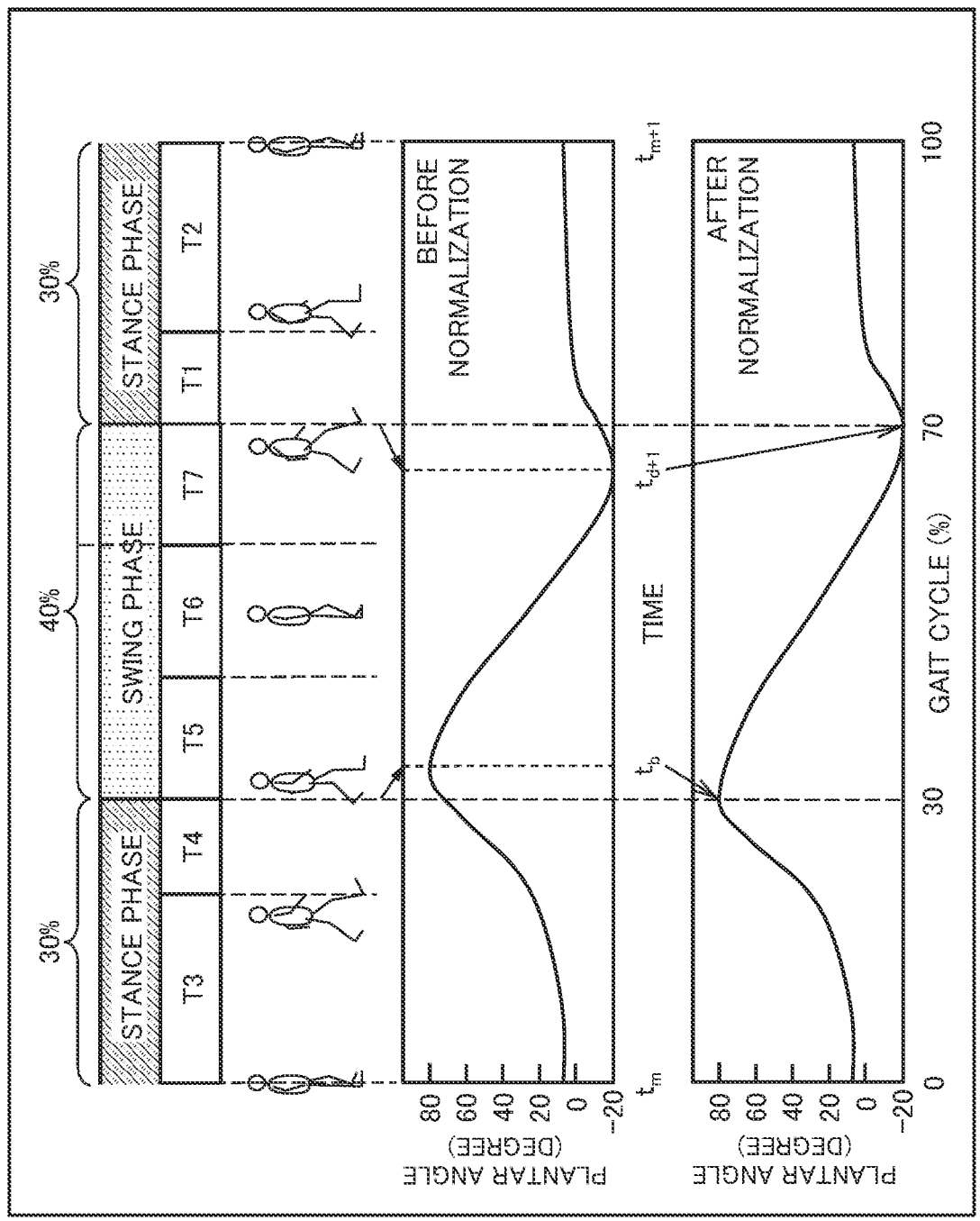
FIG. 9 is a conceptual diagram for explaining normalization by the identification device of the identification system according to the first example embodiment.

FIG. 9 is a conceptual diagram for explaining a relationship between the general gait cycle and a walking waveform of the plantar angle for one actually measured gait cycle. A schematic diagram in the upper part illustrates one gait cycle having the start point time $t_m$ of the center timing of the stance phase as the start point and the end point time $t_{m+1}$ of the center timing of the next stance phase as the end point. A graph in the middle part illustrates an actually measured walking waveform of the plantar angle for one gait cycle. The horizontal axis of the graph in the middle part represents a time for which the sensor data for calculating the plantar angle is actually measured. In the graph of the middle part, a timing at which a peak value indicating a walking event appears is shifted from the gait cycle in the upper part. A graph in the lower part illustrates a walking waveform (also referred to as a normalized waveform) of the plantar angle for one gait cycle after normalizing the timing at which the peak value indicating the walking event appears. In the graph in the lower part, a timing at which the peak value indicating the walking event appears matches the gait cycle in the upper part.

For example, the detection unit 131 detects, from the walking waveform of the plantar angle for one gait cycle, the time $t_d$ at which the walking waveform is minimized (first dorsiflexion peak) and the time $t_b$ at which the walking waveform is maximized (first plantarflexion peak) next to the first dorsiflexion peak. Furthermore, the detection unit 131 detects, from the walking waveform of the plantar angle for the next one gait cycle, a time $t_{d+1}$ at which the waveform is maximized (second dorsiflexion peak) next to the first plantarflexion peak and a time $t_{b+1}$ at which the waveform is maximized (second plantarflexion peak) next to the second dorsiflexion peak. The detection unit 131 sets a time at the midpoint between the time $t_d$ and the time $t_b$ as the start point time $t_m$ of one gait cycle. In addition, the detection unit 131 sets a time at the midpoint between the time $t_{d+1}$ and the time $t_{b+1}$ as the end point time $t_{m+1}$ of one gait cycle.

The waveform processing unit 132 cuts out the walking waveform for one gait cycle from the start point time $t_m$ to the end point time $t_{m+1}$. The waveform processing unit 132 normalizes the walking waveform of the plantar angle in order to convert a time of the actually measured walking waveform into a gait cycle. The waveform processing unit 132 normalizes walking waveforms of the accelerations, the angular velocities, and the angles in the three axial directions similarly to the plantar angle.

For example, the waveform processing unit 132 cuts out walking waveform data for one gait cycle with the time $t_m$ at the midpoint between the time $t_d$ of the first dorsiflexion peak and the time $t_b$ of the first plantarflexion peak as the start point and the time $t_{m+1}$ at the midpoint between the time $t_{d+1}$ of the second dorsiflexion peak and the time $t_{b+1}$ of the second plantarflexion peak as the end point. The waveform processing unit 132 divides the cut-out walking waveform for one gait cycle into a section from the start point time $t_m$ to the time $t_b$, a section from the time $t_b$ to the time $t_{d+1}$, and a section from the time $t_{d+1}$ to the end point time $t_{m+1}$. The waveform in the section from the start point time $t_m$ to the time $t_b$ is referred to as a first divided waveform, the waveform in the section from the time $t_b$ to the time $t_{d+1}$ is referred to as a second divided waveform, and the waveform in the section from the time $t_{d+1}$ to the end point time $t_{m+1}$ is referred to as a third divided waveform. The waveform processing unit 132 normalizes each divided waveform in such a way that the section from the start point time $t_m$ to the time $t_b$ occupies 30% of one gait cycle, the section from the time $t_b$ to the time $t_{d+1}$ occupies 40% of one gait cycle, and the section from the time $t_{d+1}$ to the end point time $t_{m+1}$ occupies 30% of one gait cycle. The waveform processing unit 132 integrates the normalized divided waveforms to generate a normalized walking waveform (also referred to as a normalized waveform) for one gait cycle. In correspondence with FIG. 7, 30% of one gait cycle corresponds to the toe off timing of (e), and 70% of one gait cycle corresponds to the heel contact timing of (a) or (g).

The identification unit 133 identifies the user based on the normalized waveform. For example, the identification unit 133 identifies the user based on the normalized waveform of at least one of the accelerations, the angular velocities, and the angles in the three axial directions. For example, the identification unit 133 compares the normalized waveform measured in advance with the normalized waveform of the user, and identifies the user based on the degree of matching between the normalized waveforms. For example, the identification unit 133 compares a feature extracted from the normalized waveform measured in advance with a feature extracted from the normalized waveform of the user, and identifies the user based on the degree of matching between the features.

For example, the identification unit 133 inputs the feature extracted from the normalized waveform based on walking of the identification target user to the trained model that has learned the feature extracted from the normalized waveform for each user, and identifies the user according to the estimation result. The identification unit 133 uses the trained model that has learned the feature extracted from the normalized walking waveform. For example, the trained model is a model trained by using features extracted from normalized waveforms of some physical quantities among a plurality of physical quantities acquired by the data acquisition device 11 for the identification target user. For example, the trained model is a model that has learned a predictor vector obtained by combining the features (also referred to as predictors) extracted from the normalized waveforms of the physical quantities measured by the data acquisition device 11 installed on the footwear of the identification target user. For example, the trained model is a model that has learned a predictor vector obtained by combining the features (predictors) extracted from the normalized waveforms of at least one of the accelerations in the three axial directions, the angular velocities in the three axial directions, and the plantar angles in the three axial directions.

Figure 10:
FIG. 10 is a conceptual diagram illustrating an example in which a trained model used by the identification device of the identification system according to the first example embodiment is generated by machine learning.
Figure 11:
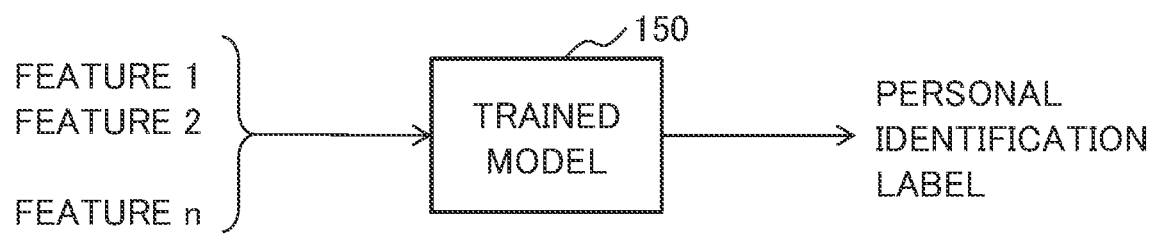
FIG. 11 is a conceptual diagram illustrating an example in which a personal identifier (ID) of a user is output when the identification device of the identification system according to the first example embodiment inputs a feature to the trained model.

FIG. 10 is a conceptual diagram illustrating an example in which a learning device 15 learns the predictor vector and a personal identification label. For example, the personal identification label is a label for identifying an individual, such as a user ID, a name, or a nickname. FIG. 11 is a conceptual diagram illustrating an example in which features 1 to n (n is a natural number) extracted from normalized waveforms of a plurality of physical quantities are input to a trained model 150 trained by the learning device 15, and the personal identification label is output.

The learning device 15 performs learning using, as training data, the predictor vector obtained by combining features (predictors) extracted from normalized waveforms based on a plurality of physical quantities and the personal identification label for personal identification. The learning device 15 generates the trained model 150 that outputs the personal identification label when the feature extracted from the normalized waveform based on the actually measured walking waveform is input by learning. For example, the learning device 15 generates the trained model 150 by supervised learning in which features extracted from a lateral acceleration, an adduction/abduction angle, and a vertical acceleration in the swing phase among a plurality of physical quantities are used as explanatory variables, and the personal identification label of the user is used as a response variable. For example, the features extracted from the lateral acceleration, the adduction/abduction angle, and the vertical acceleration in the swing phase are maximum values of the physical quantities in the swing phase. The learning device 15 is not limited to using the combination of physical quantities described herein, and it is sufficient if the predictor vector obtained by combining physical quantities that facilitate personal identification based on a gait is learned.

Operation

Next, an operation of the identification device 13 included in the identification system of the present example embodiment will be described with reference to the drawings. Hereinafter, identification processing in which the identification device 13 identifies the user and normalization processing included in the identification processing will be separately described.

Identification Processing

Figure 12:
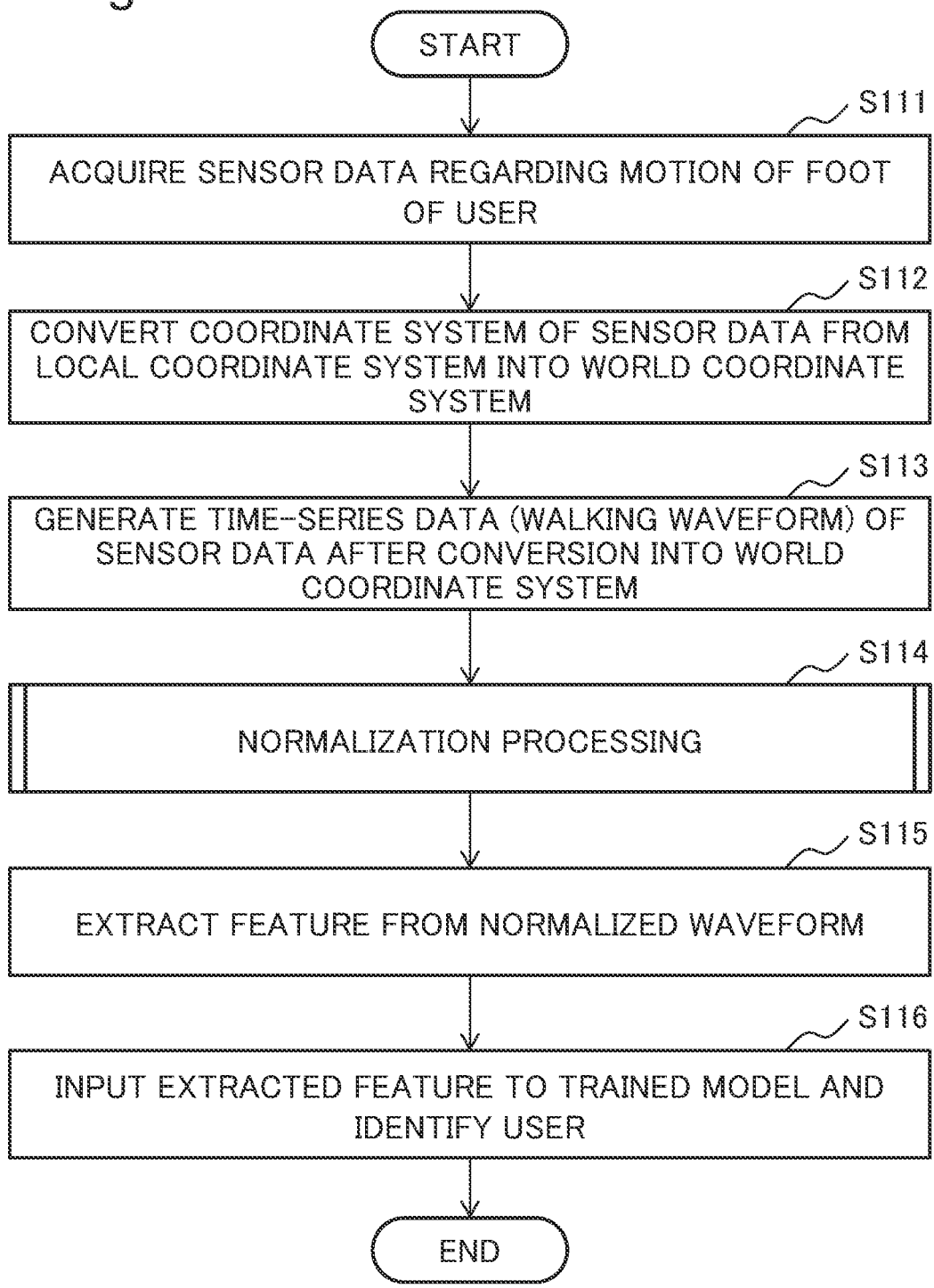
FIG. 12 is a flowchart for explaining identification processing executed by the identification device of the identification system according to the first example embodiment.

FIG. 12 is a flowchart for explaining the identification processing executed by the identification device 13. In the description with reference to the flowchart of FIG. 12, the identification device 13 will be described as an operation subject.

In FIG. 12, first, the identification device 13 acquires the sensor data regarding the motion of the foot of the user (Step S111). For example, the sensor data regarding the motion of the foot is related to the physical quantities such as the accelerations, the angular velocities, and the angles in the three axial directions.

Next, the identification device 13 converts the coordinate system of the sensor data from the local coordinate system of the data acquisition device 11 to the world coordinate system (Step S112).

Next, the identification device 13 generates the time-series data (walking waveform) of the sensor data after conversion into the world coordinate system (Step S113).

Next, the identification device 13 executes the normalization processing on the generated walking waveform (Step S114). Details of the normalization processing will be described later.

Next, the identification device 13 extracts the feature (predictor) from the normalized waveform (Step S115).

Next, the identification device 13 inputs the extracted feature (predictor) to the trained model and identifies the user (Step S116).

Normalization Processing

Figure 13:
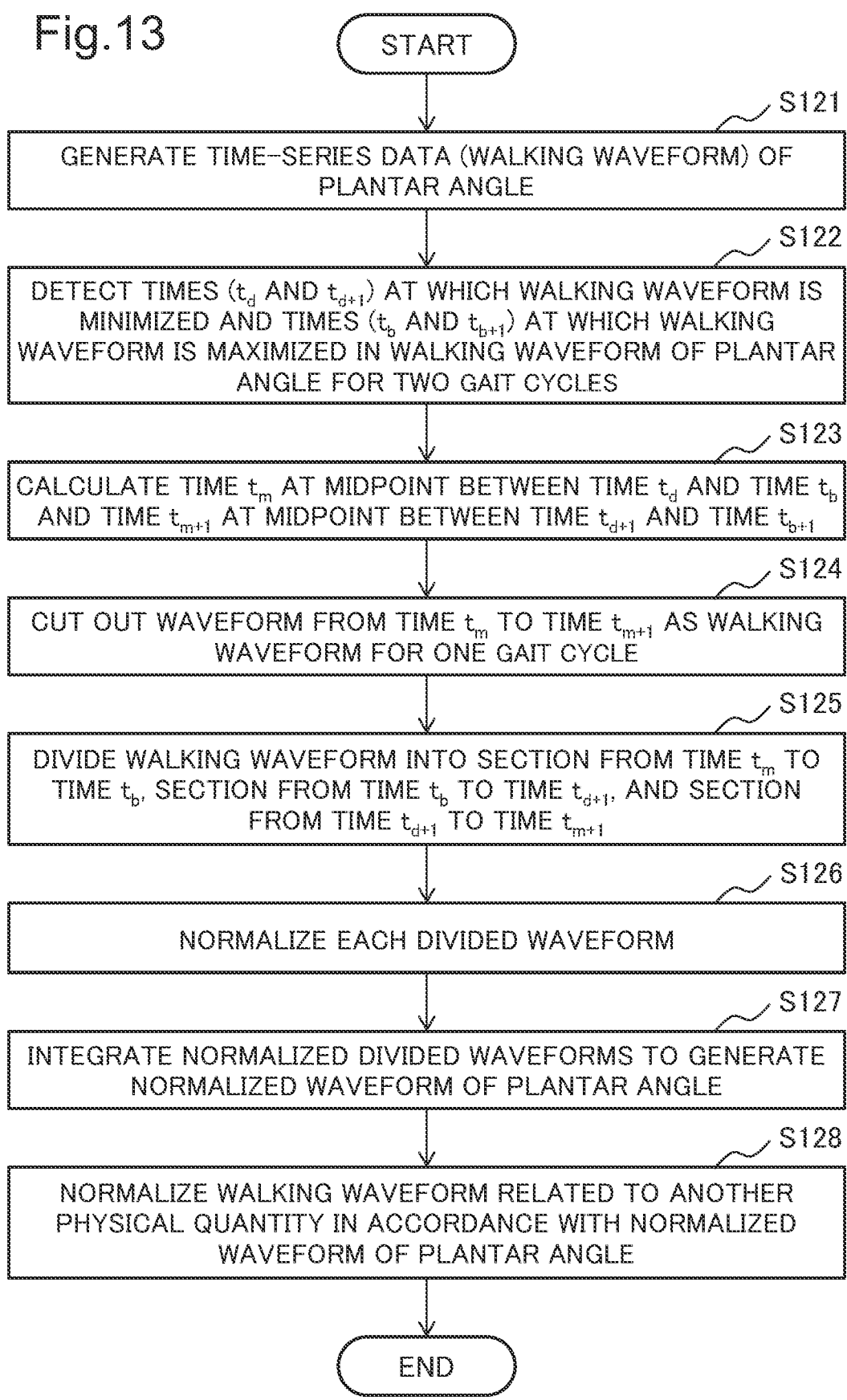
FIG. 13 is a flowchart for explaining normalization processing executed by the identification device of the identification system according to the first example embodiment.

FIG. 13 is a flowchart for explaining the normalization processing. FIG. 13 illustrates specific normalization processing of the normalization processing of Step S114 in the flowchart of FIG. 12. In the description with reference to the flowchart of FIG. 13, the identification device 13 will be described as an operation subject.

In FIG. 13, first, the identification device 13 generates the time-series data (walking waveform) of the plantar angle based on the walking waveform (Step S121).

Next, the identification device 13 detects the times (time $t_d$ and time $t_{d+1}$) at which the walking waveform of the plantar angle is minimized and the times (time $t_b$ and time $t_{b+1}$) at which the walking waveform of the plantar angle is maximized for each of two gait cycles (Step S122).

Next, the identification device 13 calculates the time $t_m$ at the midpoint between the time $t_d$ and the time $t_b$ and the time $t_{m+1}$ at the midpoint between the time $t_{d-1}$ and the time $t_{b-1}$ (Step S123).

Next, the identification device 13 cuts out a waveform from the time $t_m$ to the time $t_{m+1}$ as a walking waveform for one gait cycle (Step S124).

Next, the identification device 13 divides the walking waveform for one gait cycle into the section from the time $t_m$ to the time $t_b$, the section from the time $t_b$ to the time $t_{d+1}$, and the section from the time $t_{d+1}$ to the time $t_{m+1}$ (Step S125).

Next, the identification device 13 normalizes each divided waveform (Step S126).

Next, the identification device 13 integrates the normalized divided waveforms to generate the normalized waveform of the plantar angle (Step S127).

Next, the identification device 13 normalizes walking waveforms related to other physical quantities in accordance with the normalized waveform of the plantar angle (Step S128). The other walking waveforms include walking waveforms of accelerations, angular velocities, and angles in the three axial directions.

Verification Example

Next, a verification example of the present example embodiment will be described with an example. In this verification example, physical quantities (accelerations and angular velocities) related to a motion of a foot during walking were measured for 76 subjects, and walking waveforms of these subjects were acquired. In this verification example, an example using a normalized walking waveform (hereinafter, referred to as a normalized waveform) is compared with an example using a non-normalized walking waveform (hereinafter, referred to as a non-normalized waveform).

In this verification example, the trained model was generated using features extracted from the walking waveforms acquired when 76 subjects walk with shoes A as learning data. In this verification example, features extracted from walking waveforms acquired when 51 subjects in these subjects walk with shoes B were used as verification data. In the example using the normalized waveform, the feature extracted from the normalized waveform based on the walking waveform when the subject walks with the shoes A was used as the learning data, and the feature extracted from the normalized waveform based on the walking waveform when the subject walks with the shoes B was used as the verification data. In the example using the non-normalized waveform, the feature extracted from the walking waveform (non-normalized waveform) when the subject walks with the shoes A was used as the learning data, and the feature extracted from the walking waveform (non-normalized waveform) when the subject walks with the shoes B was used as the verification data.

Figure 14:
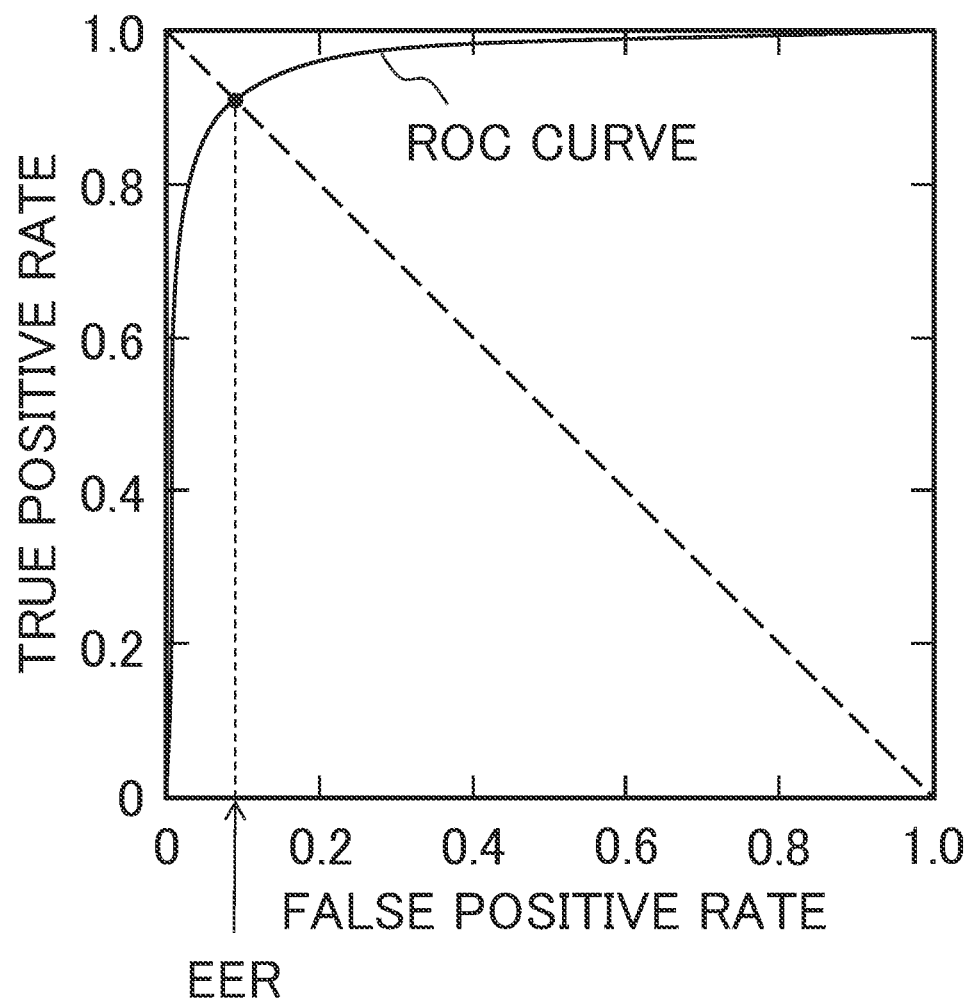
FIG. 14 is a graph for explaining an equal error rate (EER) for verifying an identification result of the identification device of the identification system according to the first example embodiment.

FIG. 14 is a graph for explaining an equal error rate (EER) used in this verification example. The EER is a measure of identification accuracy. The smaller the value of the EER, the higher the identification accuracy. A solid curve in FIG. 14 is a receiver operating characteristic (ROC) curve. In the graph of FIG. 14, a false positive rate on the horizontal axis is x, and a true positive rate on the vertical axis is y. In this verification example, an x coordinate (false positive rate) of an intersection of a straight line (broken line: y=−x+1) connecting a point (1,0) and a point (0,1) and the ROC curve corresponds to the EER.

Figure 15:
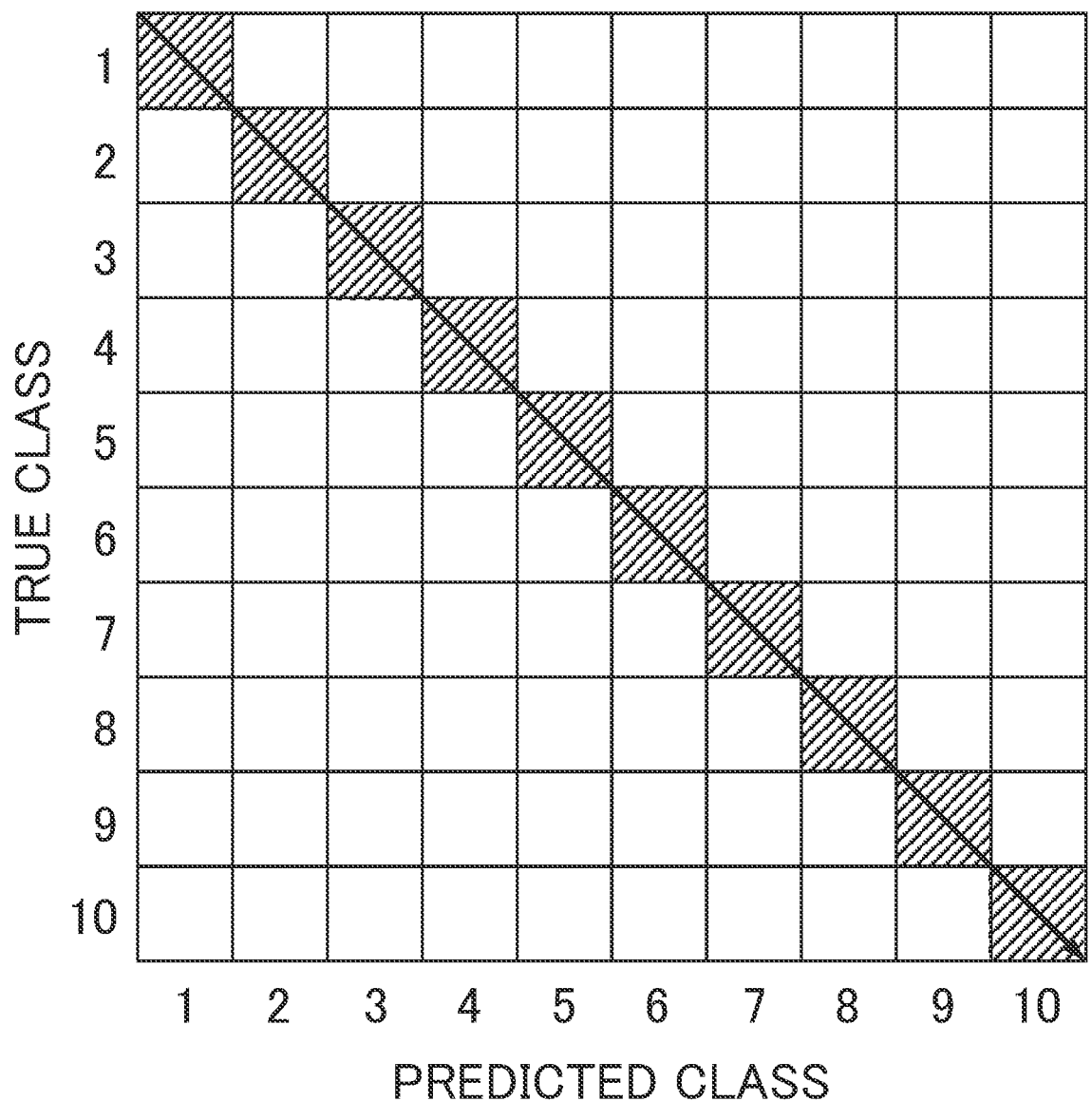
FIG. 15 is an example of a confusion matrix for explaining overall accuracy (OA) for verifying an identification result of the identification device of the identification system according to the first example embodiment.

FIG. 15 is an example of a confusion matrix for explaining overall accuracy (OA) used in this verification example. The OA corresponds to a value obtained by dividing the number of correct answers in identification by the number of pieces of data. The larger the value of the OA, the higher the identification accuracy. Instead of the OA, average accuracy (AA) obtained by adding accuracy for each category and dividing the sum by the number of categories may be used. The confusion matrix of FIG. 15 is an example of classifying the subject into classes 1 to 10. A "predicted class" is a class of the subject determined by the identification system of the present example embodiment. A "true class" is an actual class of the subject. In the confusion matrix of FIG. 15, the number of each cell is omitted. In the confusion matrix of FIG. 15, hatched cells are correct answers, and the other cells are incorrect answers. In this verification example, a value obtained by dividing the total number of hatched squares (the number of correct answers) by the number of pieces of data corresponds to the OA.

In this verification example, variables (features) of the predictors of the predictor vector are values of strengths of walking waveforms related to the accelerations, the angular velocities, and the foot angles in the three axial directions. A dimension of the predictor vector corresponds to the number of predictor vectors obtained by decomposing the walking waveform. In a case of using the walking waveforms related to the accelerations, the angular velocities, and the foot angles in the three axial directions, there are nine walking waveforms. Therefore, in a case where the walking waveform is decomposed with two points of 0% and 50%, the dimension of the predictor vector is minimized (2×9=18). For example, when a walking waveform for one gait cycle (100%) is decomposed in increments of 1%, since a predictor vector of 100 dimensions is obtained from one walking waveform, 900 predictors are obtained from the walking waveforms related to the accelerations, the angular velocities, and the plantar angles in three axial directions. For example, when a walking waveform for one gait cycle (100%) is decomposed in increments of 2%, since a predictor vector of 100 dimensions is obtained from one walking waveform, 450 predictors are obtained from the walking waveforms related to the accelerations, the angular velocities, and the plantar angles in three axial directions.

Figure 16:
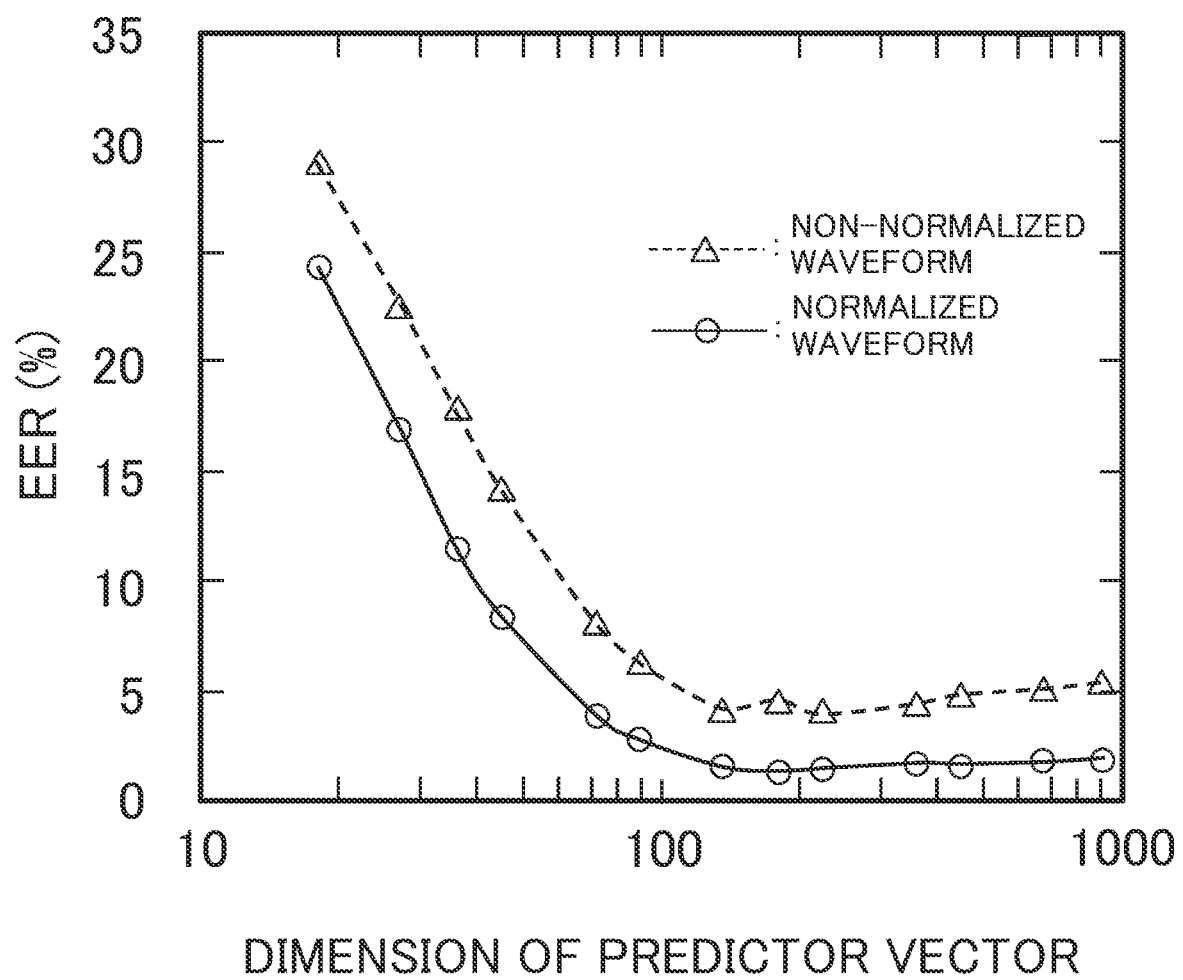
FIG. 16 is a graph illustrating an example in which an identification result of the identification device of the identification system according to the first example embodiment is verified using the EER.

FIG. 16 is a graph illustrating a result of verifying the EER in a case where the feature extracted from the walking waveform of the subject walking with the shoes B is input to the trained model trained using the feature extracted from the walking waveform of the subject walking with the shoes A. In FIG. 16, the EER in the result of the verification using the feature extracted from the normalized waveform is indicated by a solid line, and the EER in the result of the verification using the feature extracted from the non-normalized waveform is indicated by a broken line. As illustrated in FIG. 16, the EER was smaller in a case of using the normalized waveform than in a case of using the non-normalized waveform. That is, for the EER, a better result was obtained when using the normalized waveform as in the present example embodiment.

Figure 17:
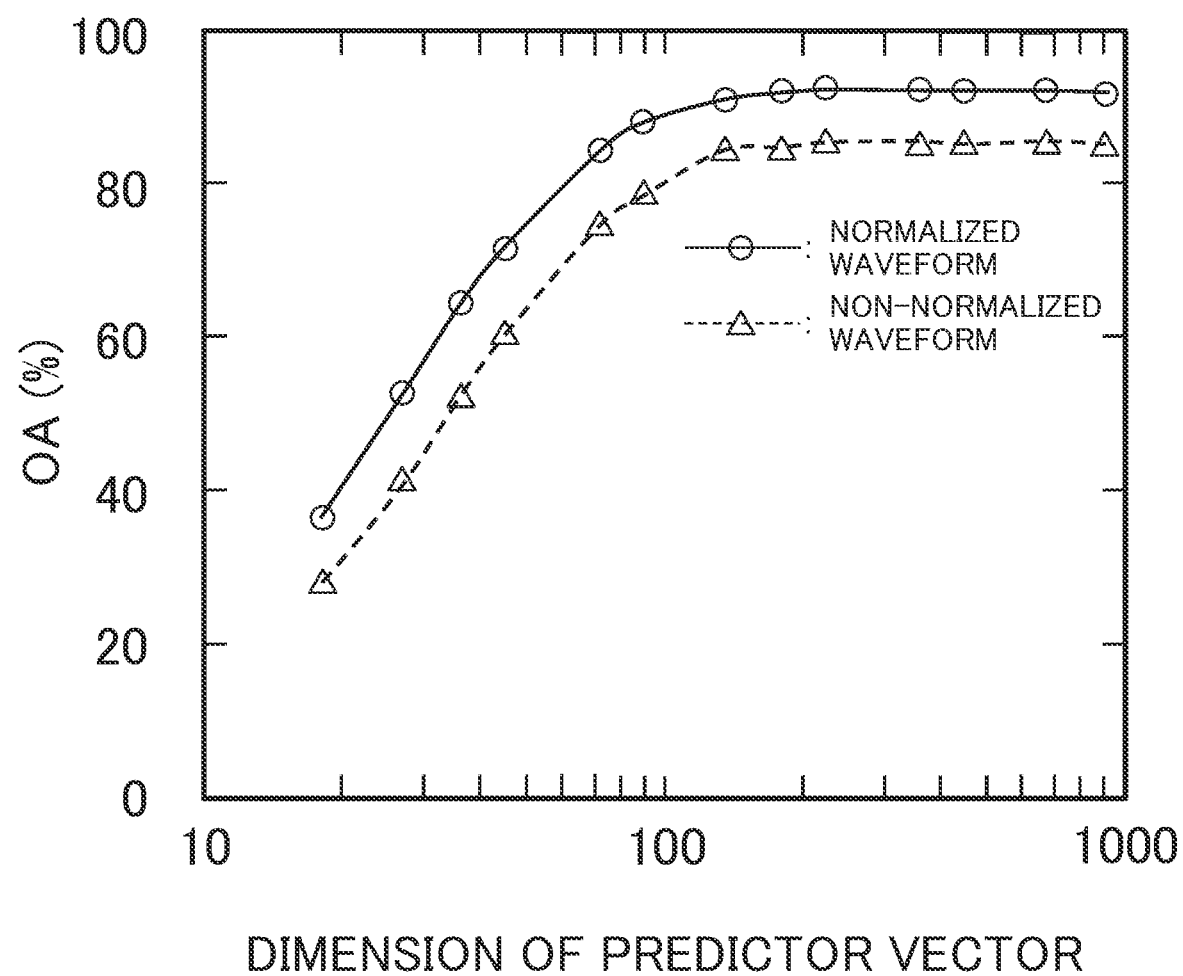
FIG. 17 is a graph illustrating an example in which an identification result of the identification device of the identification system according to the first example embodiment is verified using the OA.

FIG. 17 is a graph illustrating a result of verifying the OA in a case where the feature extracted from the walking waveform of the subject walking with the shoes B is input to the trained model trained using the feature extracted from the walking waveform of the subject walking with the shoes A. In FIG. 17, the OA in the result of the verification using the feature extracted from the normalized waveform is indicated by a solid line, and the OA in the result of the verification using the feature extracted from the non-normalized waveform is indicated by a broken line. As illustrated in FIG. 17, the OA was higher in a case of using the normalized waveform than in a case of using the non-normalized waveform. That is, also for the OA, a better result was obtained when using the normalized waveform as in the present example embodiment.

In this verification example, an example in which the user is identified by inputting the predictor extracted from the walking waveform based on walking with the shoes B to the trained model that has learned the walking waveform based on walking with the shoes A has been described. As described above, even in a case where the shoes are different, the EER was lower and the OA was higher in a case of using the normalized waveform than in a case of using the non-normalized waveform. That is, according to the present example embodiment, even in a case where the shoes are different, it is easy to identify an individual based on a gait.

As described above, the identification system according to the present example embodiment includes the data acquisition device, the mobile terminal, and the identification device. The identification device includes the detection unit, the waveform processing unit, and the identification unit. The detection unit detects a walking event from a walking waveform of a user. The waveform processing unit normalizes the walking waveform based on the detected walking event to generate a normalized waveform. The identification unit identifies the user based on the normalized waveform.

In one aspect of the present example embodiment, the waveform processing unit normalizes the walking waveform of the plantar angle to generate the normalized waveform. The waveform processing unit normalizes the walking waveform of each of the accelerations in the three axial directions, the angular velocities in the three axial directions, and the angles in the three axial directions in accordance with the generated normalized waveform of the plantar angle to generate the normalized waveform of each of the accelerations in the three axial directions, the angular velocities in the three axial directions, and the angles in the three axial directions.

In one aspect of the present example embodiment, the detection unit detects the first dorsiflexion peak, the first plantarflexion peak, the second dorsiflexion peak, and the second plantarflexion peak as the walking events from the walking waveform of the plantar angle for two gait cycles. The waveform processing unit cuts out a walking waveform for one gait cycle from a start point time at the midpoint between a first time of the first dorsiflexion peak and a second time of the first plantarflexion peak to an end point time at the midpoint between a third time of the second dorsiflexion peak and a fourth time of the second plantarflexion peak. The waveform processing unit divides the cut-out walking waveform for one gait cycle into the first divided waveform from the start point time to the second time, the second divided waveform from the second time to the third time, and the third divided waveform from the third time to the end point time. The waveform processing unit normalizes each of the first divided waveform, the second divided waveform, and the third divided waveform. The waveform processing unit generates the normalized waveform of the plantar angle by integrating the normalized first divided waveform, second divided waveform, and third divided waveform. For example, the waveform processing unit normalizes each of the first divided waveform, the second divided waveform, and the third divided waveform in such a way that, in one gait cycle, the first divided waveform has a fraction of 30%, the second divided waveform has a fraction of 40%, and the third divided waveform has a fraction of 30%.

In one aspect of the present example embodiment, the identification unit inputs, to the trained model, the feature extracted from the normalized waveform of at least one of accelerations, angular velocities, and angles of an identification target user in the three axial directions, and identifies the identification target user. The identification unit uses the trained model trained using, as the training data, a predictor vector including a feature extracted from a normalized waveform of at least one of accelerations, angular velocities, and angles of a registration target user in the three axial directions, and an identifier of the registration target user.

According to the present example embodiment, an influence of the footwear on the walking waveform can be reduced by normalizing the walking waveform based on the walking event. As a result, according to the present example embodiment, it is possible to identify an individual based on a gait regardless of the type of footwear.

Second Example Embodiment

Next, an identification system (also referred to as an authentication system) according to a second example embodiment will be described with reference to the drawings. The present example embodiment is different from the first example embodiment in that authentication is performed using an identification result of an identification device and control according to the authentication result is performed. The authentication system according to the present example embodiment performs personal identification by measuring a feature (also referred to as a gait) included in a walking pattern of a user and analyzing the measured gait. Then, the identified user is authenticated, and a control target device is controlled according to the authentication result. Hereinafter, the "user" means an authentication target person of the authentication system according to the present example embodiment.

Configuration

Figure 18:
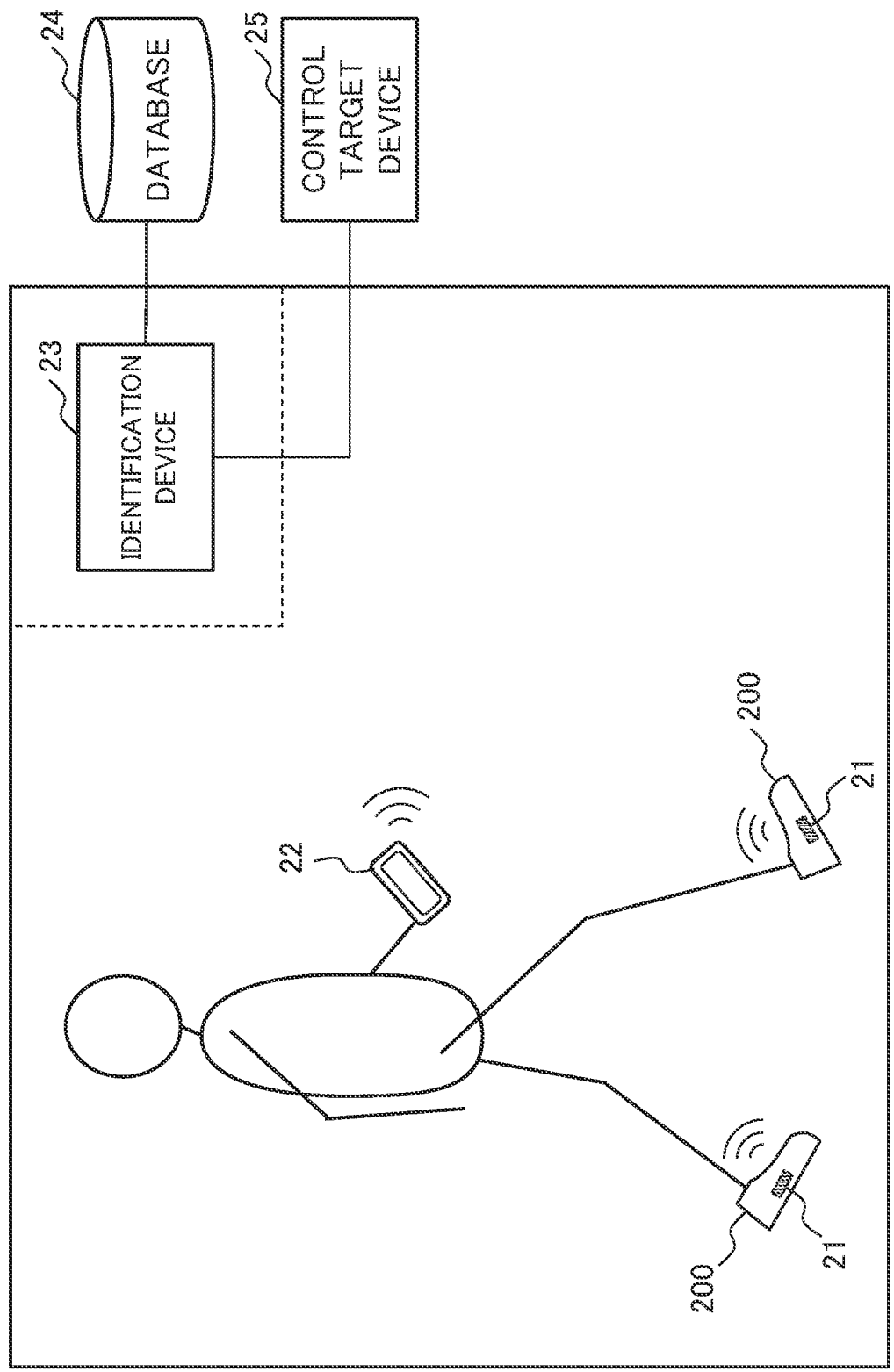
FIG. 18 is a conceptual diagram illustrating an example of a configuration of an authentication system according to a second example embodiment.

FIG. 18 is a conceptual diagram for explaining an overall configuration of the authentication system according to the present example embodiment. The authentication system according to the present example embodiment includes a data acquisition device 21 installed in footwear such as a shoe 200, a mobile terminal 22 carried by a user, and an identification device 23. FIG. 18 illustrates a database 24 and a control target device 25 in addition to the authentication system according to the present example embodiment. The identification device 23 is connected to the database 24 and the control target device 25. Authentication information of an authentication target user is registered in the database 24. The control target device 25 is a device controlled according to the authentication result. The authentication system according to the present example embodiment may include the database 24 and the control target device 25.

The data acquisition device 21 acquires sensor data regarding a motion of a foot of the user. The data acquisition device 21 transmits the acquired sensor data to the identification device 23 via the mobile terminal 22. The identification device 23 identifies the user based on the received sensor data. The user identified by the identification device 23 is collated with the authentication information stored in the database 24, and is subjected to some authentication according to the collation result. Once the user is authenticated, the identification device 23 controls the control target device 25 according to the authentication result. The data acquisition device 21 and the mobile terminal 22 have the same configurations as those of the data acquisition device 11 and the mobile terminal 12 of the identification system according to the first example embodiment. Therefore, the data acquisition device 21 and the mobile terminal 22 will not be described, and the identification device 23 will be described below.

Identification Device

Figure 19:
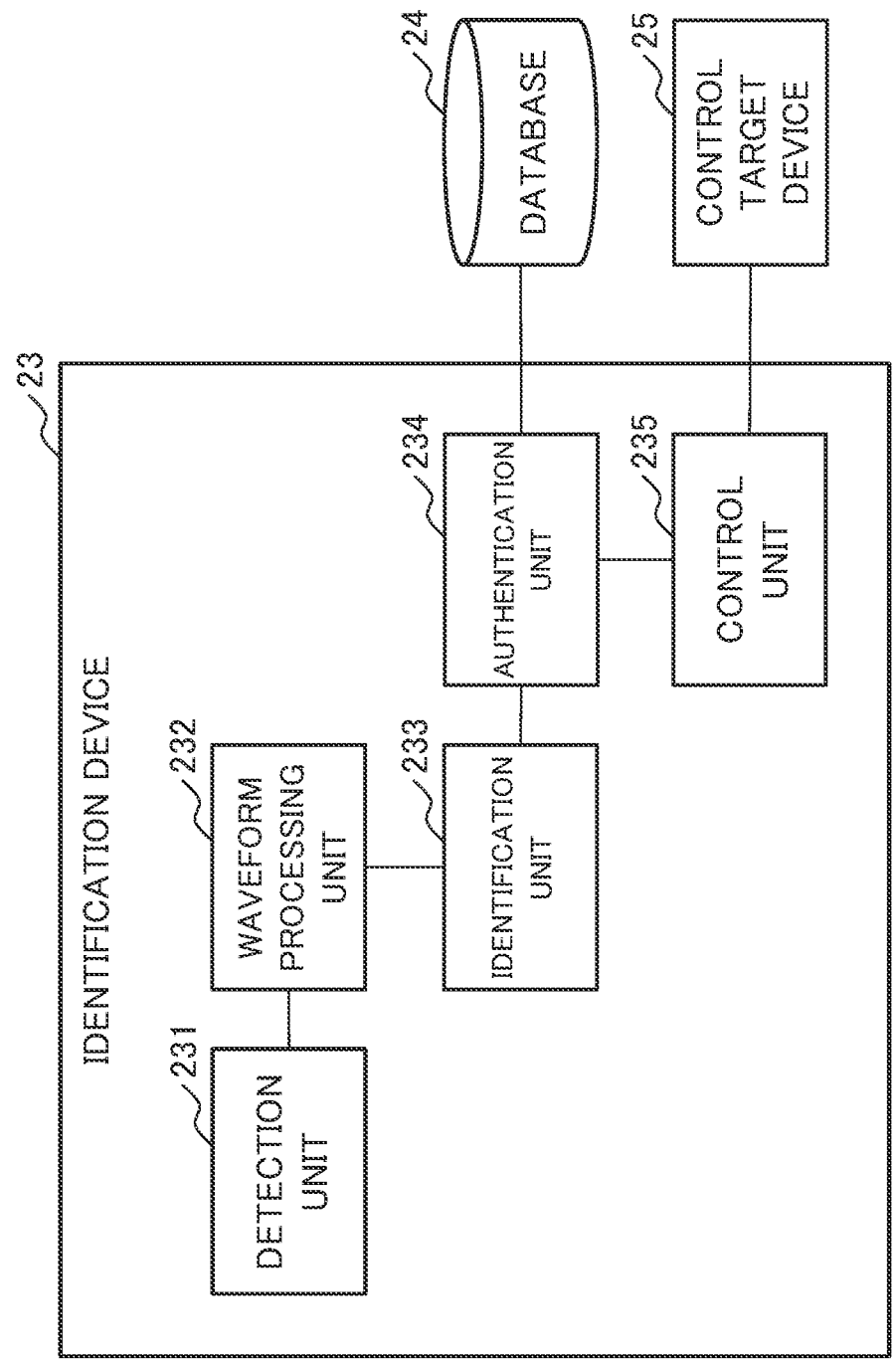
FIG. 19 is a block diagram illustrating an example of a configuration of an identification device according to the second example embodiment.

FIG. 19 is a block diagram illustrating an example of a detailed configuration of the identification device 23. The identification device 23 includes a detection unit 231, a waveform processing unit 232, an identification unit 233, an authentication unit 234, and a control unit 235.

The detection unit 231 acquires the sensor data from the data acquisition device 21. The detection unit 231 converts a coordinate system of the acquired sensor data from the local coordinate system to the world coordinate system. The detection unit 231 generates a walking waveform by using the sensor data whose coordinate system is converted to the world coordinate system. The detection unit 231 generates a walking waveform related to accelerations, angular velocities, and angles in the three axial directions. The detection unit 231 generates a walking waveform of the plantar angle by using time-series data of the accelerations and the angular velocities.

The detection unit 231 detects, from the walking waveform of the plantar angle, a time $t_d$ at which the plantar angle is minimized (dorsiflexion peak) and a time $t_b$ at which the plantar angle is maximized (plantarflexion peak) next to the dorsiflexion peak. Furthermore, the detection unit 231 detects a time $t_{d+1}$ of a dorsiflexion peak next to the plantarflexion peak and a time $t_{b+1}$ of a plantarflexion peak next to the dorsiflexion peak. The detection unit 231 sets a time at the midpoint between the time $t_d$ and the time $t_b$ as the start point time $t_m$ of one gait cycle. In addition, the detection unit 231 sets a time at the midpoint between the time $t_{d+1}$ and the time $t_{b+1}$ as the end point time $t_{m+1}$ of one gait cycle.

The waveform processing unit 232 cuts out a walking waveform for one gait cycle with the time tm at the center of the stance phase as the start point. That is, the waveform processing unit 232 cuts out a walking waveform for one gait cycle with the time $t_m$ at the center of the stance phase as the start point and the time $t_{m+1}$ at the center of the next stance phase as the end point. The waveform processing unit 232 normalizes the walking waveform of the plantar angle in order to convert a time of the actually measured walking waveform into a gait cycle. The waveform processing unit 232 normalizes walking waveforms of the accelerations, the angular velocities, and the angles in the three axial directions similarly to the plantar angle.

The identification unit 233 identifies the user based on the normalized walking waveform (also referred to as a normalized waveform). For example, the identification unit 233 identifies the user based on the normalized waveform of at least one of the accelerations, the angular velocities, and the angles in the three axial directions. For example, the identification unit 233 compares the normalized waveform measured in advance with the normalized waveform of the user, and identifies the user based on the degree of matching between the normalized waveforms. For example, the identification unit 233 compares a feature extracted from the normalized waveform measured in advance with a feature extracted from the normalized waveform of the user, and identifies the user based on the degree of matching between the features. For example, the identification unit 233 inputs the feature extracted from the normalized waveform of the user to the trained model that has learned the feature extracted from the normalized waveform for each user, and identifies the user according to the estimation result.

The authentication unit 234 performs authentication of the user according to the identification result of the identification unit 233. The authentication unit 234 performs collation to check whether the user identified by the identification unit 233 is registered in the authentication information stored in the database 24. In a case where the authentication of the user identified by the identification unit 233 has succeeded, the authentication unit 234 outputs, to the control unit 235, an instruction to control the control target device 25. On the other hand, in a case where the authentication of the user identified by the identification unit 233 has not succeeded, the authentication unit 234 does not output, to the control unit 235, the instruction to control the control target device 25.

The control unit 235 controls the control target device 25 in accordance with the control instruction from the authentication unit 234. In a case where only the authentication is performed, the control unit 235 may be omitted.

For example, in a case where the control target device 25 is an auto-lock system of a door, the control unit 235 unlocks the door in response to a control instruction from the authentication unit 234. For example, in a case where the control target device 25 is a computer, the control unit 235 enables access to the computer in response to a control instruction from the authentication unit 234. For example, in a case where the control target device 25 is an automobile, the control unit 235 unlocks a door of the automobile or starts an engine of the automobile in response to a control instruction from the authentication unit 234. In a case where the authentication of the user identified by the identification unit 233 has not succeeded, the control unit 235 may perform control in such a way as to cause the auto-lock system to lock the door, disable access to the computer, or not to start the engine of the automobile. The control example of the control target device 25 described here is an example, and does not limit the control in the present example embodiment.

Operation

Next, an operation of the identification device 23 included in the authentication system according to the present example embodiment will be described with reference to the drawings. Hereinafter, authentication processing of performing authentication of the user identified by the identification device 23 will be described. User identification processing executed by the identification device 23 and normalization processing included in the identification processing are the same as those in the first example embodiment, and thus, a description thereof will be omitted.

Authentication Processing

Figure 20:
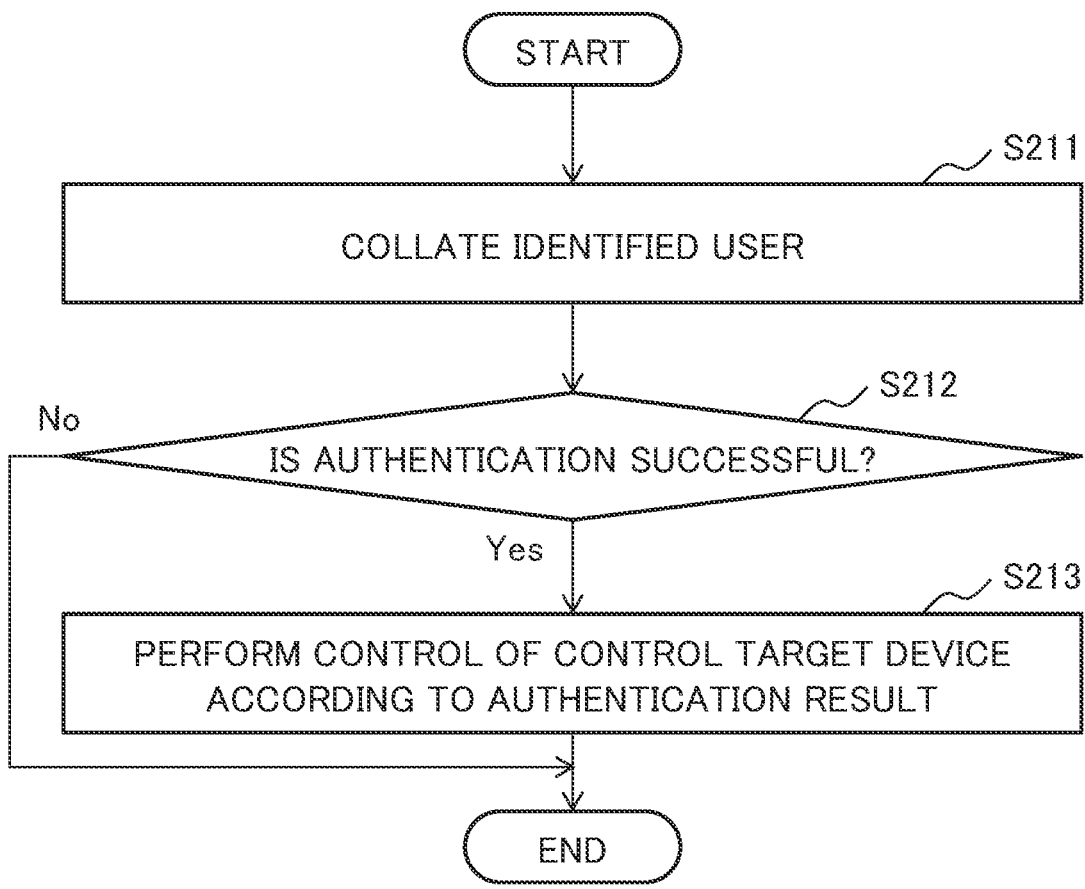
FIG. 20 is a flowchart for explaining authentication processing executed by the identification device according to the second example embodiment.

FIG. 20 is a flowchart for explaining the authentication processing. The authentication processing of FIG. 20 is processing subsequent to Step S116 of FIG. 12. In the description with reference to the flowchart of FIG. 20, the identification device 23 will be described as an operation subject.

In FIG. 20, first, the identification device 23 accesses the database 24 and collates the identified user (Step S211).

Here, in a case where the authentication result is successful (Yes in Step S212), the identification device 23 controls the control target device 25 according to the authentication result (Step S213). On the other hand, in a case where the authentication result is not successful (No in Step S212), the identification device 23 does not control the control target device 25. In a case where the authentication result is not successful (No in Step S212), the identification device 23 may perform, on the control target device 25, control that is to be performed when the authentication result is not successful.

Application Example

Next, an application example of the authentication system according to the present example embodiment will be described with reference to the drawings. In this application example, an automatic door or an auto-lock system of an automobile will be described as an example. In this application example, an example in which an authentication region is set in the vicinity of an automatic door or an automobile on which the control target device 25 is mounted, and authentication of a user who has entered the authentication region is performed will be described.

Application Example 1

Figure 21:
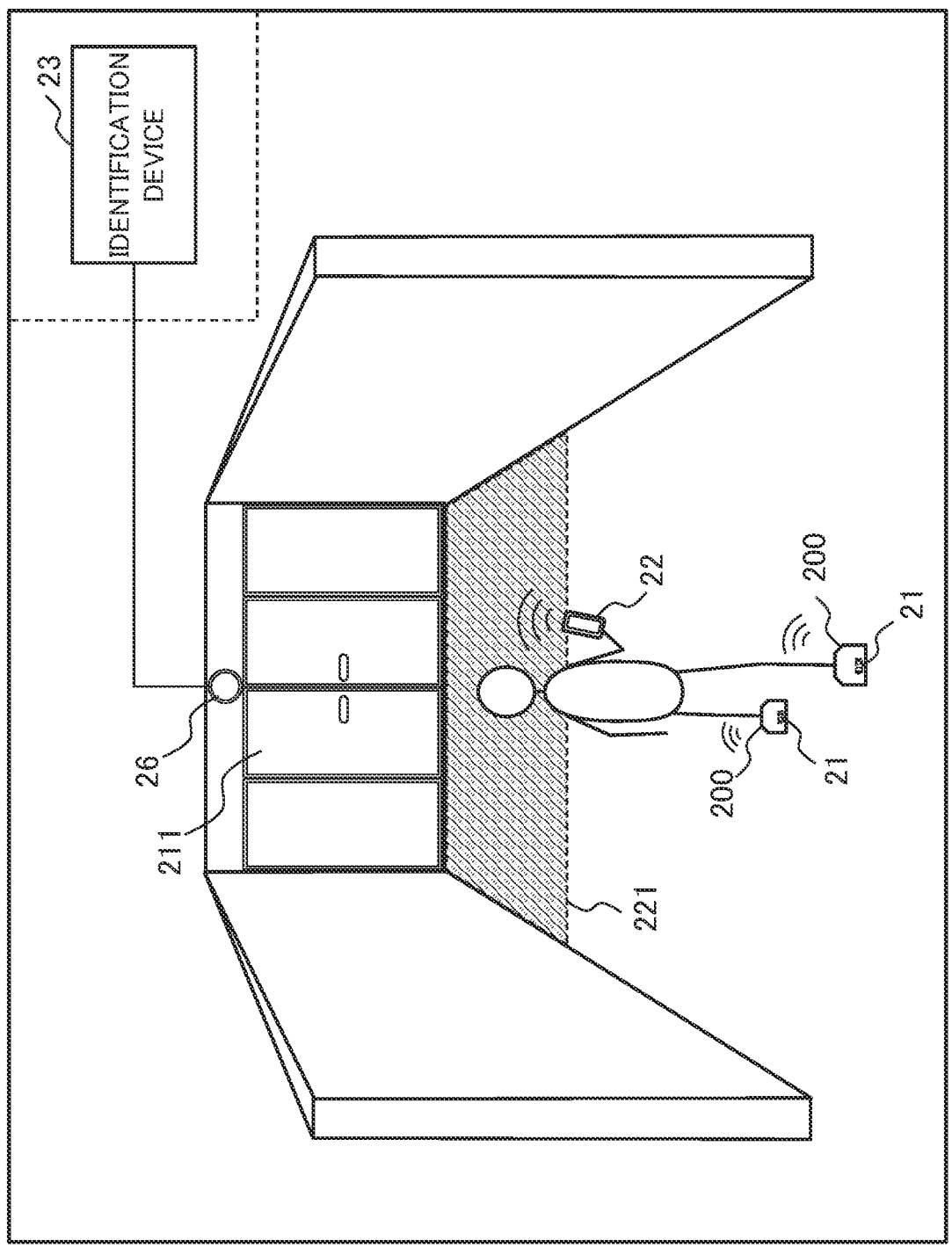
FIG. 21 is a conceptual diagram for explaining Application Example 1 of the authentication system according to the second example embodiment.

FIG. 21 is a conceptual diagram for explaining Application Example 1 in which the authentication system according to the present example embodiment is applied to an auto-lock system of an automatic door 211. FIG. 21 illustrates a state in which the user carrying the mobile terminal 22 and walking with the shoes 200 each on which the data acquisition device 21 is mounted approaches the automatic door 211. The mobile terminal 22 does not need to be held by the user's hand, and it is sufficient if the mobile terminal 22 is carried by the user. Alternatively, a reception device (not illustrated) that receives the sensor data transmitted from the data acquisition device 21 may be installed near the automatic door 211 instead of carrying the mobile terminal 22 by the user. FIG. 21 illustrates a camera 26 that captures an image of the vicinity of the automatic door 211. For example, the camera 26 is sensitive to a visible region or an infrared region, and transmits a captured image to the identification device 23 or the like.

It is assumed that the control target device 25 (not illustrated) that controls unlocking/locking of the automatic door 211 is mounted on the automatic door 211. In addition, it is assumed that the automatic door 211 is provided with an opening/closing mechanism (not illustrated) that controls opening/closing of the automatic door 211 in response to detection of a pedestrian when the automatic door 211 is unlocked. The opening/closing mechanism of the automatic door 211 may be controlled by the control target device 25. A range in which user authentication is to be performed (authentication region 221) is set in the vicinity of the automatic door 211. For example, it is sufficient if the authentication region 221 is set according to a positional relationship between the automatic door 211 and the mobile terminal 22 based on position information obtained by a global positioning system (GPS) or the like. In addition, the authentication region 221 may be set based on an image captured by the camera 26 provided in the vicinity of the automatic door 211.

Once the user enters the authentication region 221, the identification device 23 generates a normalized waveform from the walking waveform of the sensor data received via the mobile terminal 22. The identification device 23 identifies the user by using the generated normalized waveform. The identification device 23 accesses the database 24 (not illustrated) and collates the identified user. For example, in a case where the authentication of the user is successful, the identification device 23 controls the control target device 25. The control target device 25 unlocks the automatic door 211 under the control of the identification device 23. For example, in a case where the authentication of the user is not successful, the identification device 23 may control the control target device 25 to lock the automatic door 211.

This application example is suitable for a scene where a user who is allowed to enter is limited, such as a residence such as a multiplex house or an apartment, a specific facility such as a hospital or a factory, a public facility such as a school, or an important facility. In particular, since user authentication can be performed regardless of the type of footwear, this application example is suitable for use scenes where the footwear of the user is frequently changed. For example, in nursing care welfare facilities, medical sites, factories, and the like, a change to various shoes and movement in a wide range often occur, and thus this application example is suitable. For example, if this application example is introduced to a food processing factory or the like, it is not necessary to input a passcode or authenticate a fingerprint or a palm print with a hand touching a food. Therefore, the worker easily moves in a state where sufficient security is obtained. For example, if this application example is introduced to a medical site, the medical staff can easily move safely in a state where sufficient security is obtained.

For example, the user authentication may be performed by combining authentication based on a face image of the user included in the image captured by the camera 26 installed in the vicinity of the automatic door 211 with gait authentication by the identification device 23. For example, an image capturing range of the camera 26 may be set to be farther than the authentication region 221, and the identification device 23 may be set to perform the gait authentication when the face authentication based on the face image is successful. For example, the image capturing range of the camera 26 may be set within the range of the authentication region 221, and the face authentication based on the face image may be set to be performed in a case where the gait authentication by the identification device 23 is successful. For example, the automatic door 211 may be set to be unlocked in a case where both the gait authentication by the identification device 23 and the face authentication based on the face image are successful. By combining the gait authentication by the identification device 23 and the face authentication based on the face image captured by the camera 26, security can be further improved.

Application Example 2

Figure 22:
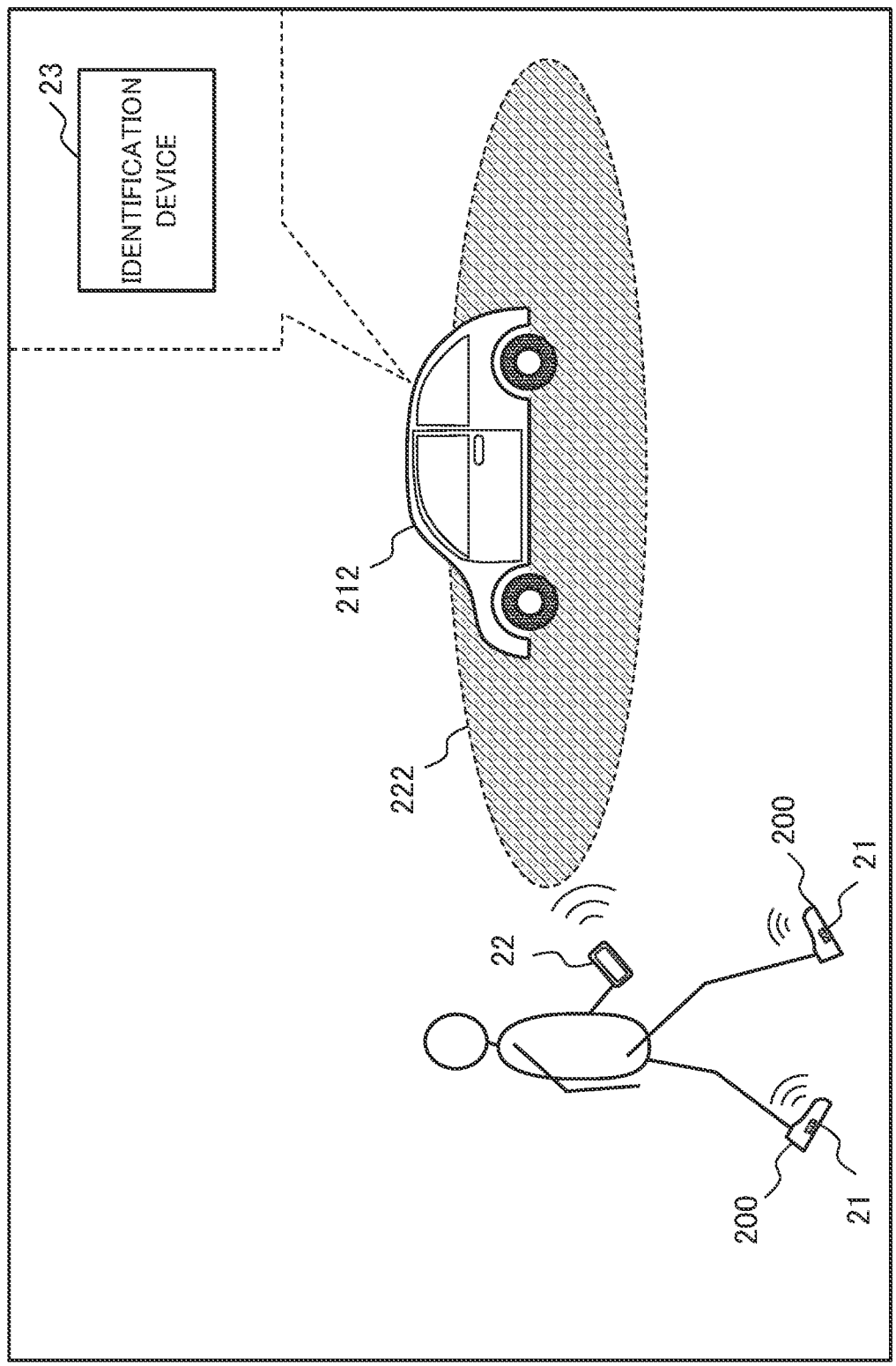
FIG. 22 is a conceptual diagram for explaining Application Example 2 of the authentication system according to the second example embodiment.

FIG. 22 is a conceptual diagram for explaining Application Example 2 in which the authentication system according to the present example embodiment is applied to a key of an automobile 212. FIG. 22 illustrates a state in which the user carrying the mobile terminal 22 and walking with the shoes 200 each of on which the data acquisition device 21 is mounted approaches the automobile 212. The mobile terminal 22 does not need to be held by the user's hand, and it is sufficient if the mobile terminal 22 is carried by the user. Alternatively, a reception device (not illustrated) that receives the sensor data transmitted from the data acquisition device 21 may be installed in the automobile 212 instead of carrying the mobile terminal 22 by the user.

It is assumed that the control target device 25 (not illustrated) that controls unlocking/locking of the doors of the automobile 212 is mounted on the automobile 212. A range in which user authentication is to be performed (authentication region 222) is set in the vicinity of the automobile 212. For example, it is sufficient if the authentication region 222 is set according to a positional relationship between the automobile 212 and the mobile terminal 22 based on position information obtained by a GPS or the like. In addition, the authentication region 222 may be set based on an image captured by a camera (not illustrated) provided in the automobile 212.

Once the user enters the authentication region 222, the identification device 23 generates a normalized waveform from the walking waveform of the sensor data received via the mobile terminal 22. The identification device 23 identifies the user by using the generated normalized waveform. The identification device 23 accesses the database 24 (not illustrated) and collates the identified user. For example, in a case where the authentication of the user is successful, the identification device 23 controls the control target device 25. The control target device 25 unlocks a door of the automobile 212 under the control of the identification device 23. For example, in a case where the authentication of the user is not successful, the identification device 23 may control the control target device 25 to lock the door of the automobile 212.

According to this application example, user authentication can be performed even in a case where a road surface of a parking place of the automobile 212 is different. Examples of the road surface of the parking place include asphalt, soil, and gravel. A walking waveform of a person changes according to the condition of the road surface, but if the walking waveform is normalized, it is possible to cope with a change in condition of the road surface to some extent.

For example, security can be further improved by combining the gait authentication by the identification device 23 and the key. For example, if setting is made in such a way that only a user who has succeeded in the gait authentication can open and close the door and start the engine by using the key, it is possible to prevent theft of the automobile 212 and driving of the automobile 212 by a person who does not hold a driver's license. For example, there may be a case where the gait authentication cannot be made because a road surface condition of a place where the automobile 212 is parked is poor, and the user cannot approach the automobile 212 in a normal walking state. In preparation for such a case, setting may be made in such a way that the door of the automobile 212 can be opened and closed only with the key without performing the gait authentication, by inputting a predetermined passcode or the like to the mobile terminal 22.

As described above, the identification system according to the present example embodiment includes the data acquisition device, the mobile terminal, and the identification device. The identification device includes the detection unit, the waveform processing unit, the identification unit, the authentication unit, and the control unit. The detection unit detects a walking event from a walking waveform of a user. The waveform processing unit normalizes the walking waveform based on the detected walking event to generate a normalized waveform. The identification unit identifies the user based on the normalized waveform. The authentication unit accesses the database in which the authentication information is stored to perform authentication of the user identified by the identification device. The control unit controls the control target device according to the authentication result of the authentication unit.

According to the present example embodiment, an influence of the footwear on the walking waveform can be reduced by normalizing the walking waveform based on the walking event. As a result, according to the present example embodiment, it is possible to identify an individual based on a gait regardless of the type of footwear. Further, the identified individual can be authenticated.

Third Example Embodiment

Figure 23:
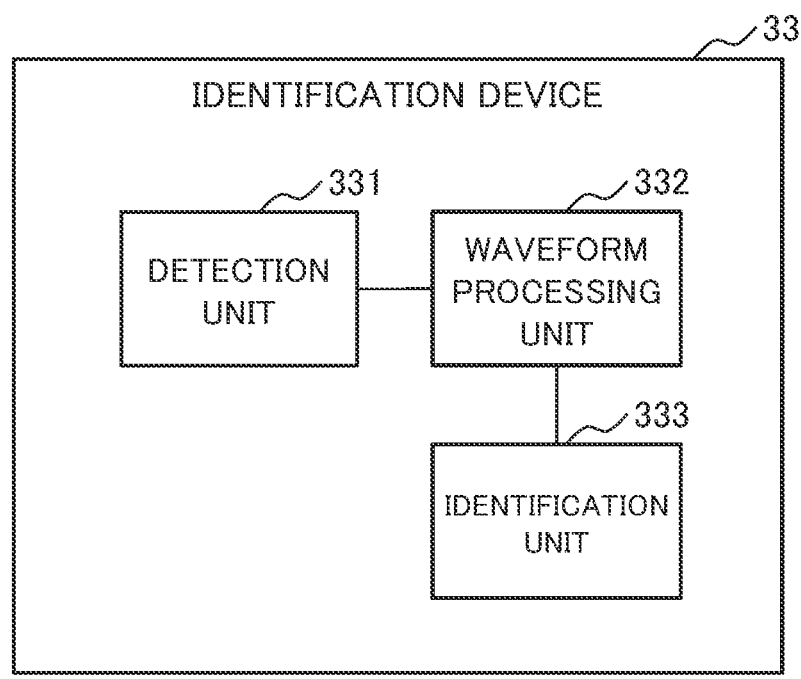
FIG. 23 is a block diagram illustrating an example of a configuration according to a third example embodiment.

Next, an identification device according to a third example embodiment will be described with reference to the drawings. The identification device according to the present example embodiment has a configuration in which the identification devices of the first to second example embodiments are simplified. FIG. 23 is a block diagram illustrating an example of a configuration of the identification device 33 according to the present example embodiment. The identification device 33 includes a detection unit 331, a waveform processing unit 332, and an identification unit 333.

The detection unit 331 detects a walking event from a walking waveform of a user. The waveform processing unit 332 normalizes the walking waveform based on the detected walking event to generate a normalized waveform. The identification unit 333 identifies the user based on the normalized waveform.

According to the present example embodiment, it is possible to identify an individual based on a gait regardless of the type of footwear by normalizing the walking waveform.

Hardware

Here, a hardware configuration for implementing the identification device according to each example embodiment of the present invention will be described using an information processing device 90 of FIG. 24 as an example. The information processing device 90 in FIG. 24 is a configuration example for implementing the identification device of each example embodiment, and does not limit the scope of the present invention.

Figure 24:
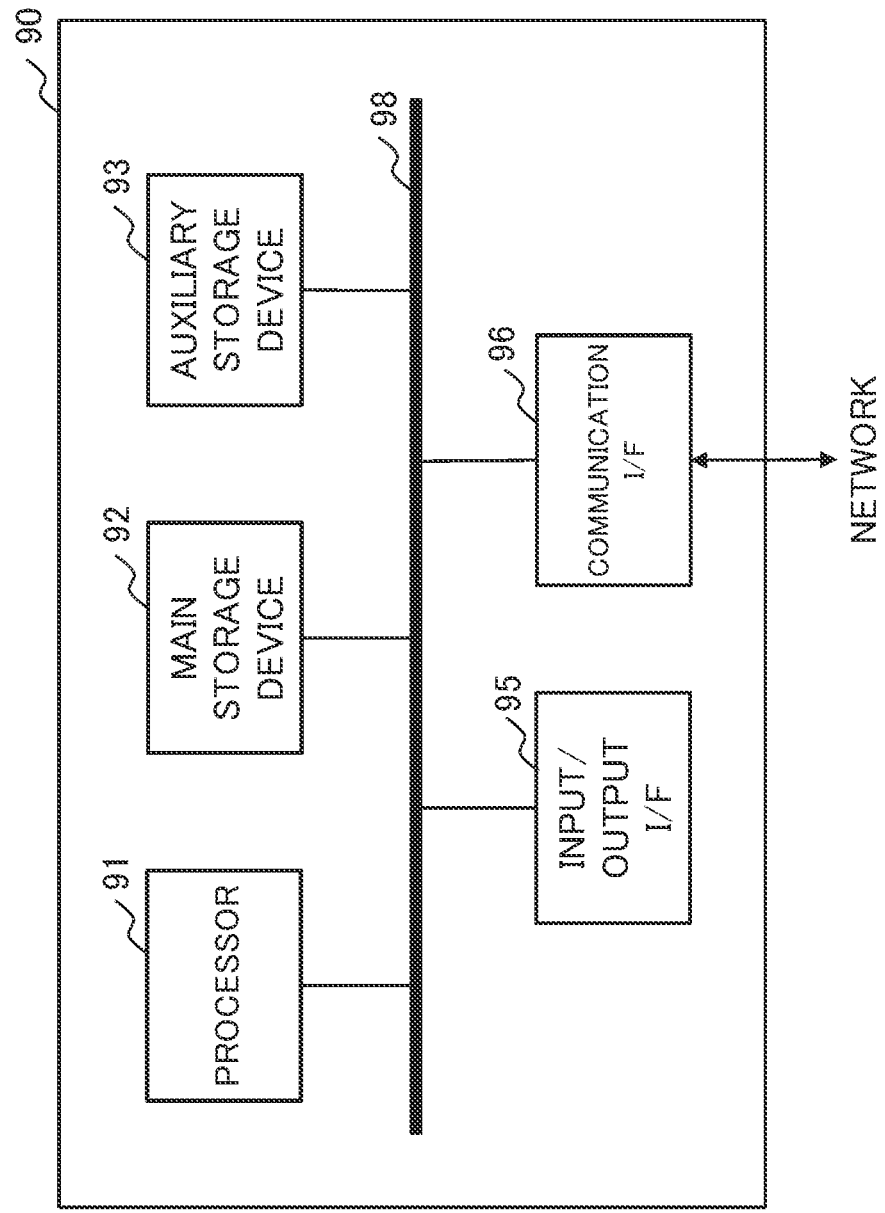
FIG. 24 is a block diagram illustrating an example of a hardware configuration for implementing the identification device of each example embodiment.

As illustrated in FIG. 24, the information processing device 90 includes a processor 91, a main storage device 92, an auxiliary storage device 93, an input/output interface 95, and a communication interface 96. In FIG. 24, the interface is abbreviated as an I/F. The processor 91, the main storage device 92, the auxiliary storage device 93, the input/output interface 95, and the communication interface 96 are data-communicably connected to each other via a bus 98. In addition, the processor 91, the main storage device 92, the auxiliary storage device 93, and the input/output interface 95 are connected to a network such as the Internet or an intranet via the communication interface 96.

The processor 91 loads a program stored in the auxiliary storage device 93 or the like to the main storage device 92 and executes the loaded program. In the present example embodiment, it is sufficient if a software program installed in the information processing device 90 is used. The processor 91 executes processing in the identification device according to the present example embodiment.

The main storage device 92 has a region to which the program is loaded. The main storage device 92 may be a volatile memory such as a dynamic random access memory (DRAM). In addition, a nonvolatile memory such as a magnetoresistive random access memory (MRAM) may be configured and added as the main storage device 92.

The auxiliary storage device 93 stores various pieces of data. The auxiliary storage device 93 is implemented by a local disk such as a hard disk or a flash memory. Various pieces of data may be stored in the main storage device 92, and the auxiliary storage device 93 may be omitted.

The input/output interface 95 is an interface for connecting the information processing device 90 and a peripheral device. The communication interface 96 is an interface for connecting to an external system or device through a network such as the Internet or an intranet based on a protocol or a specification. The input/output interface 95 and the communication interface 96 may be shared as an interface connected to an external device.

An input device such as a keyboard, a mouse, or a touch panel may be connected to the information processing device 90 as necessary. These input devices are used to input information and settings. In a case where the touch panel is used as the input device, it is sufficient if a display screen of a display device also serves as the interface of the input device. Data communication between the processor 91 and the input device may be performed via the input/output interface 95.

The information processing device 90 may be provided with a display device for displaying information. In a case where the display device is provided, the information processing device 90 preferably includes a display control device (not illustrated) for controlling display of the display device. The display device may be connected to the information processing device 90 via the input/output interface 95.

An example of the hardware configuration for implementing the identification device according to each example embodiment of the present invention has been described above. The hardware configuration of FIG. 24 is an example of the hardware configuration for executing arithmetic processing in the identification device according to each example embodiment, and does not limit the scope of the present invention. In addition, a program for causing a computer to execute processing related to the identification device according to each example embodiment also falls within the scope of the present invention. Further, a program recording medium having the program according to each example embodiment recorded therein also falls within the scope of the present invention. The recording medium can be implemented by, for example, an optical recording medium such as a compact disc (CD) or a digital versatile disc (DVD). Furthermore, the recording medium may be implemented by a semiconductor recording medium such as a universal serial bus (USB) memory or a secure digital (SD) card, a magnetic recording medium such as a flexible disk, or another recording medium. In a case where the program executed by the processor is recorded in a recording medium, the recording medium corresponds to the program recording medium.

Any combination of the components of the identification device of each example embodiment is possible. In addition, the components of the identification device of each example embodiment may be implemented by software or may be implemented by a circuit.

While the present invention has been particularly shown and described with reference to the example embodiments thereof, the present invention is not limited to these example embodiments. It will be understood by those of ordinary skill in the art that various changes in form and details may be made therein without departing from the spirit and scope of the present invention as defined by the claims.

REFERENCE SIGNS LIST 11, 21 Data acquisition device
12, 22 Mobile terminal
13, 23 Identification device
24 Database
25 Control target device
111 Acceleration sensor
112 Angular velocity sensor
113 Control unit
115 Data transmission unit
131, 231, 331 Detection unit
132, 232, 332 Waveform processing unit
133, 233, 333 Identification unit
234 Authentication unit
235 Control unit

What is claimed is:

1. An identification device comprising:
one or more memories storing instructions; and
one or more processors configured to execute the instructions to:
detect a walking event from a walking waveform of a user;
normalize the walking waveform based on the detected walking event to generate a normalized waveform;
identify the user based on the normalized waveform;
wherein generating the normalized waveform includes:
normalize a plantar angle walking waveform to generate the normalized waveform used for identifying the user; and
normalize walking waveforms of each of accelerations in three axial directions, angular velocities in the three axial directions, and angles in the three axial directions in accordance with the generated normalized plantar angle walking waveform to generate normalized waveforms of each of the accelerations in the three axial directions, the angular velocities in the three axial directions, and the angles in the three axial directions;
wherein the normalized waveform used for identifying the user comprises at least the generated normalized plantar angle walking waveform and the normalized waveforms of each of the accelerations in the three axial directions, the angular velocities in the three axial directions, and the angles in the three axial directions.

2. The identification device according to claim 1,
wherein the one or more processors are configured to execute the instructions to:
detect a first dorsiflexion peak, a first plantarflexion peak, a second dorsiflexion peak, and a second plantarflexion peak from the walking waveform of a plantar angle for two gait cycles;
set a time at a midpoint between a first time of the first dorsiflexion peak and a second time of the first plantarflexion peak as a start point time;
set a time at a midpoint between a third time of the second dorsiflexion peak and a fourth time of the second plantarflexion peak as an end point time;
cut out the walking waveform for one gait cycle from the start point time to the end point time;
divide the cut-out walking waveform for one gait cycle into a first divided waveform from the start point time to the second time, a second divided waveform from the second time to the third time, and a third divided waveform from the third time to the end point time;
normalize each of the first divided waveform, the second divided waveform, and the third divided waveform; and
integrate the normalized first divided waveform, second divided waveform, and third divided waveform to generate the normalized waveform of the plantar angle.

3. The identification device according to claim 2,
wherein the one or more processors are configured to execute the instructions to normalize each of the first divided waveform, the second divided waveform, and the third divided waveform in such a way that, in one gait cycle, the first divided waveform has a fraction of 30%, the second divided waveform has a fraction of 40%, and the third divided waveform has a fraction of 30%.

4. The identification device according to claim 1,
wherein the one or more processors are configured to execute the instructions to input a feature extracted from the normalized waveform of at least one of accelerations, angular velocities, and angles of an identification target user in three axial directions to a trained model trained using, as training data, a predictor vector including the feature extracted from the normalized waveform of at least one of accelerations, angular velocities, and angles of a registration target user in the three axial directions and an identifier of the registration target user, and identifies the identification target user.

5. The identification device according to claim 4,
wherein the one or more processors are configured to execute the instructions to access a database storing authentication information to perform authentication of the user identified by the identification device.

6. The identification device according to claim 5,
wherein the one or more processors are configured to execute the instructions to control a control target device according to an authentication result.

7. An identification method executed by a computer, the identification method comprising:
detecting a walking event from a walking waveform of a user;
normalizing the walking waveform based on the detected walking event to generate a normalized waveform; and
identifying the user based on the normalized waveform;
wherein generating the normalized waveform includes:
normalizing a plantar angle walking waveform to generate the normalized waveform used for identifying the user; and
normalizing walking waveforms of each of accelerations in three axial directions, angular velocities in the three axial directions, and angles in the three axial directions in accordance with the generated normalized plantar angle walking waveform to generate normalized waveforms of each of the accelerations in the three axial directions, the angular velocities in the three axial directions, and the angles in the three axial directions;
wherein the normalized waveform used for identifying the user comprises at least the generated normalized plantar angle walking waveform and the normalized waveforms of each of the accelerations in the three axial directions, the angular velocities in the three axial directions, and the angles in the three axial directions.

8. A non-transitory program recording medium recorded with a program for causing a computer to execute:
processing of detecting a walking event from a walking waveform of a user;
processing of normalizing the walking waveform based on the detected walking event to generate a normalized waveform; and
processing of identifying the user based on the normalized waveform;
wherein generating the normalized waveform includes:
normalizing a plantar angle walking waveform to generate the normalized waveform used for identifying the user; and
normalizing walking waveforms of each of accelerations in three axial directions, angular velocities in the three axial directions, and angles in the three axial directions in accordance with the generated normalized plantar angle walking waveform to generate normalized waveforms of each of the accelerations in the three axial directions, the angular velocities in the three axial directions, and the angles in the three axial directions;
wherein the normalized waveform used for identifying the user comprises at least the generated normalized plantar angle walking waveform and the normalized waveforms of each of the accelerations in the three axial directions, the angular velocities in the three axial directions, and the angles in the three axial directions.

* * * * *